US006909771B2

(12) United States Patent
Waggener et al.

(10) Patent No.: US 6,909,771 B2
(45) Date of Patent: Jun. 21, 2005

(54) THREE COMPONENT X-RAY BONE DENSITOMETRY

(75) Inventors: Robert G. Waggener, Natalia, TX (US); Elizabeth Wieckowska, San Antonio, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 9 days.

(21) Appl. No.: 10/719,783

(22) Filed: Nov. 20, 2003

(65) Prior Publication Data

US 2004/0190679 A1 Sep. 30, 2004

Related U.S. Application Data

(60) Provisional application No. 60/428,300, filed on Nov. 22, 2002.

(51) Int. Cl.[7] .............................................. G01N 23/06
(52) U.S. Cl. .......................................... 378/54; 378/55
(58) Field of Search .............................. 378/51, 54, 55, 378/56

(56) References Cited

U.S. PATENT DOCUMENTS 5,673,298 A * 9/1997 Mazess ......................... 378/54
6,064,716 A * 5/2000 Siffert et al. .................. 378/53

OTHER PUBLICATIONS

Blake GM et al., Dual energy x–ray absorptiometry: The effects of beam hardening on bone density measurements. *Med. Phys.* 19(2),: 459–465 (1992).
Cheng S, et al., Bone density of calcaneus and fractures in 75 and 80 year old men and women. *Osteoporosis Int.* 4:48–54, 1994.
Consensus Development Conference. Diagnosis, prophylaxis, and treatment of osteoporosis. *Am J Med* 94: 646–50 (1993).
Farrell TJ, et al., Triple photon absorptiometry cannot correct for fat inhomogenities in lumbar spine bone mineral measurements. *Clin. Phys. Physiol. Meas.* 11(1):77–84 (1990).
Farrell, et al. "The error due to fat inhomogenity in lumbar spine bone mineral measurements." *Clin. Phys. Physiol. Meas.* 10:57–64 (1989).
Genant, et al., "Noninvasive assessment of bone mineral and structure: state of the art." *J Bone Miner Res.* 11:707–730 (1996).
Gosfield E, et al., Evaluating bone mineral density in osteoporosis. *Am J of Phys Med and Rehab*, 79(3): 283–291 (2000).
Greenfield MA., Current status of physical measurements of the skeleton. *Med. Phys.* 19(6): 1349–1357 (1992).
Jonson R., et al., Triple–photon energy absortiometry in the measurement of bone mineral. *Acta Radiol.* 29:461–464 (1988).
Kalender W.A., A phantom for standardization and quality control in spinal bone mineral measurements by QCT and DXA: Design considerations and specifications. *Med. Phys.* 19(3) (1992).

(Continued)

*Primary Examiner*—Edward J. Glick
*Assistant Examiner*—Chih-Cheng Glen Kao
(74) *Attorney, Agent, or Firm*—Needle & Rosenberg, P.C.

(57) ABSTRACT

The in vivo three component areal density composition of a patient along a transmitted x-ray beam is derived by raster-scanning a collimated x-ray beam across a bony region of the patient, with each point scanned at different energies, and using matrix equations with a priori spectra information to solve for the relative areal density of soft tissue, fat and bone.

5 Claims, 42 Drawing Sheets

OTHER PUBLICATIONS

Kotzki, et al., "Theoretical and experimental limits of triple photon energy absorptiometry in the measurement of bone mineral." *Phys. Med. Biol.* 36(4):429–437 (1991).

Larnach TA, et al., Reproducibility of lateral spine scans using dual energy x–ray absorptiometry. *Calcif Tissue Int.* 67–255–8 (1992).

Lehmann, et al., "Generalized image combinations in dual KVp digital radiography." *Med. Phys.* 8:659–667 (1981).

Lilley J, et al., An investigation of spinal bone mineral measurement laterally: a normal range for UK women. *Br J Radiol.* 67:157–161 (1994).

Michael, et al., "Monte Carlo modeling of an extended DXA technique." *Phys. Med. Biol.* 43:2583–2596 (1998).

Resnick D, et al., Diagnosis of bone and joint disorders. *Osteoporosis, ed.* D.Resnick and G.Niwayama, pp. 2026–2085. W.B. Saunders, 1988.

Smith MA, et al., Comparison between $^{153}$Gd and $^{241}$Am, $^{137}$Cs for dual–photon absorptiometry of the spine. *Phys. Meal. Biol.* 28(6):709–721 (1983).

Sutcliffe, "A review of in vivo experimental methods to determine the composition of the human body." *Phys. Med. Biol.* 41:791–833 (1996).

Svendsen, et al. "Impact of soft tissue on in–vivo accuracy of bone mineral measurements in the spine, hip and forearm: a human cadaver study." *J Bone Miner Res* 10: 868–73 (1995).

Tothill P., Methods of bone mineral measurement. *Phys. Med. Biol.* 34(5):544–568 (1989).

Tothill, et al, "Errors due to non–uniform distribution of fat in dual x–ray absorptiometry of the lumbar spine." *Br J Radiol* 65:807–13 (1992).

Vogel JM, et al., The clinical relevance of calcaneus bone mineral measurement: A review. *Bone Miner.* 5:35–58 (1988).

Wahner HW, et al., Assessment of bone mineral. *J of Nucl. Med.* 25(10):1134–1141 (1984).

Wahner, et al., "Dual–photon Gd–153 absortiometry of bone." *Radiology* 156: 203 (1985).

Wang, et al., "Body fat from body density: underwater weighting vs. dual–photon absortiometry." *Am. J. Physiol.* 256 (1989).

Wishnia G., Challenges in the care of adults with osteoporosis. *Geriatric nursing* 22(3):160–164 (2001).

* cited by examiner

```
FOR kg1=Lower Limit kg1 to Upper Limit kg2 step kg1step(usually 0.001 or 0.0005)
    FOR kg3=Upper Limit kg3 to Lower Limit kg3 step -kg3(usually 0.001 or
0.0005)
        LET kg2=1-kg1-kg3
        IF kg2>Then Kg2 input lower limit and kg2<Kg2 Upper Limit then
          CALL loop
        END IF
      NEXT kg3
    NEXT kg1

SUB loop
  LET rhoxg(p5,1)=kg1*sumrhoxg
  LET rhoxg(p5,2)=kg2*sumrhoxg
  LET rhoxg(p5,3)=kg3*sumrhoxg
  LET sumdif=0
  FOR i=Energy lower limit to Energy Higher Limit step 1 keV
      LET argguess(p5,i)=murhosofttissue(i)*rhoxg(p5,1)
      LET argguess(p5,i)=argguess(p5,i)+murhofat(i)*rhoxg(p5,2)
      LET argguess(p5,i)=argguess(p5,i)+murhobone100(i)*rhoxg(p5,3)
      LET sumdif=sumdif+abs(argpoly2(p5,i)-argguess(p5,i))
  NEXT i
  IF sumdif<sumdifbest(p5) then
    LET sumdifbest(p5)=sumdif
    LET kg1best(p5)=kg1
    LET kg2best(p5)=kg2
    LET kg3best(p5)=kg3
    LET rhoxgbest(p5,1)=rhoxg(p5,1)
    LET rhoxgbest(p5,2)=rhoxg(p5,2)
    LET rhoxgbest(p5,3)=rhoxg(p5,3)
  END IF
END SUB
```

FIG. 6

| Description | C Carbon | O Oxygen | H Hydrogen | N Nitrogen | Ca Calcium | P Phosphorus | Cl Chlorine | Physical density |
|---|---|---|---|---|---|---|---|---|
| Adipose | 0.724 | 0.155 | 0.094 | 0.023 | 0.0025 | 0 | 0.002 | 0.967 |
| Muscle | 0.697 | 0.168 | 0.091 | 0.021 | 0.022 | 0 | 0.001 | 1.062 |
| Trabecular Bone 100 mg/cc | 0.622 | 0.203 | 0.084 | 0.017 | 0.057 | 0.014 | 0.0016 | 1.084 |

FIG. 7

| Phantom number | Areal densities (cm²/g) | | |
| --- | --- | --- | --- |
| | Muscle | Adipose tissue | Bone |
| Phantom 1 | 21.24 | 2.901 | 1.084 |
| Phantom 2 | 15.93 | 2.901 | 1.084 |
| Phantom 3 | 15.93 | 6.769 | 1.084 |
| Phantom 4 | 15.93 | 2.901 | 2.168 |
| Phantom 5 | 10.62 | 2.901 | 1.084 |

FIG. 10

| keV | Mean | SD | CV |
|---|---|---|---|
| 36.5 | 766 | 8.75 | 0.0114 |
| 37.5 | 793 | 8.91 | 0.0112 |
| 38.5 | 820 | 9.06 | 0.0110 |
| 39.5 | 858 | 9.26 | 0.0108 |
| 40.5 | 867 | 9.31 | 0.0107 |
| 41.5 | 892 | 9.44 | 0.0106 |
| 42.5 | 902 | 9.50 | 0.0105 |
| 43.5 | 892 | 9.44 | 0.0106 |
| 44.5 | 898 | 9.48 | 0.0106 |
| 45.5 | 888 | 9.42 | 0.0106 |
| 46.5 | 885 | 9.40 | 0.0106 |
| 47.5 | 890 | 9.43 | 0.0106 |
| 48.5 | 880 | 9.38 | 0.0107 |
| 49.5 | 848 | 9.21 | 0.0109 |
| 50.5 | 844 | 9.19 | 0.0109 |
| 51.5 | 842 | 9.18 | 0.0109 |
| 52.5 | 797 | 8.93 | 0.0112 |
| 53.5 | 795 | 8.91 | 0.0112 |
| 54.5 | 772 | 8.78 | 0.0114 |
| 55.5 | 745 | 8.63 | 0.0116 |
| 56.5 | 728 | 8.53 | 0.0117 |
| 57.5 | 869 | 9.32 | 0.0107 |
|  |  | Average | 0.0109 |

FIG. 14

| keV | Mean | SD | CV |
|---|---|---|---|
| 36.5 | 10232 | 41.30 | 0.0040 |
| 37.5 | 10561 | 41.95 | 0.0040 |
| 38.5 | 10973 | 42.76 | 0.0039 |
| 39.5 | 11286 | 43.37 | 0.0038 |
| 40.5 | 11494 | 43.77 | 0.0038 |
| 41.5 | 11612 | 43.99 | 0.0038 |
| 42.5 | 11800 | 44.35 | 0.0038 |
| 43.5 | 11918 | 44.57 | 0.0037 |
| 44.5 | 11870 | 44.48 | 0.0037 |
| 45.5 | 11862 | 44.46 | 0.0037 |
| 46.5 | 11756 | 44.26 | 0.0038 |
| 47.5 | 11795 | 44.34 | 0.0038 |
| 48.5 | 11546 | 43.87 | 0.0038 |
| 49.5 | 11444 | 43.67 | 0.0038 |
| 50.5 | 11206 | 43.22 | 0.0039 |
| 51.5 | 11082 | 42.98 | 0.0039 |
| 52.5 | 10688 | 42.21 | 0.0039 |
| 53.5 | 10549 | 41.93 | 0.0040 |
| 54.5 | 10220 | 41.27 | 0.0040 |
| 55.5 | 9953 | 40.73 | 0.0041 |
| 56.5 | 9695 | 40.20 | 0.0041 |
| 57.5 | 11264 | 43.53 | 0.0038 |
|  |  | Average | 0.0039 |

FIG. 16

| keV | μ/ρ experim. | μ/ρ theoret. | Ratio | $\sigma_{(\mu/\rho)}$ |
|---|---|---|---|---|
| 36.5 | 0.2891 | 0.2913 | 0.993 | 0.0045 |
| 37.5 | 0.2821 | 0.2828 | 0.998 | 0.0043 |
| 38.5 | 0.2754 | 0.2750 | 1.001 | 0.0042 |
| 39.5 | 0.2690 | 0.2680 | 1.004 | 0.0041 |
| 40.5 | 0.2628 | 0.2620 | 1.003 | 0.0040 |
| 41.5 | 0.2570 | 0.2567 | 1.001 | 0.0039 |
| 42.5 | 0.2516 | 0.2518 | 0.999 | 0.0037 |
| 43.5 | 0.2464 | 0.2472 | 0.997 | 0.0037 |
| 44.5 | 0.2415 | 0.2428 | 0.994 | 0.0036 |
| 45.5 | 0.2369 | 0.2388 | 0.992 | 0.0034 |
| 46.5 | 0.2326 | 0.2350 | 0.990 | 0.0034 |
| 47.5 | 0.2287 | 0.2314 | 0.988 | 0.0035 |
| 48.5 | 0.2250 | 0.2281 | 0.987 | 0.0035 |
| 49.5 | 0.2217 | 0.2250 | 0.985 | 0.0035 |
| 50.5 | 0.2186 | 0.2222 | 0.984 | 0.0036 |
| 51.5 | 0.2159 | 0.2197 | 0.982 | 0.0036 |
| 52.5 | 0.2134 | 0.2173 | 0.982 | 0.0036 |
| 53.5 | 0.2113 | 0.2150 | 0.983 | 0.0036 |
| 54.5 | 0.2095 | 0.2128 | 0.984 | 0.0036 |
| 55.5 | 0.2080 | 0.2107 | 0.987 | 0.0037 |
| 56.5 | 0.2067 | 0.2087 | 0.991 | 0.0037 |
| 57.5 | 0.2058 | 0.2068 | 0.995 | 0.0037 |

FIG. 20

| keV | $\mu/\rho$ experim. | $\mu/\rho$ theoret. | Ratio | $\sigma_{(\mu/\rho)}$ |
|---|---|---|---|---|
| 36.5 | 0.2505 | 0.2520 | 0.994 | 0.0062 |
| 37.5 | 0.2467 | 0.2466 | 1.000 | 0.0060 |
| 38.5 | 0.2429 | 0.2417 | 1.005 | 0.0059 |
| 39.5 | 0.2393 | 0.2371 | 1.009 | 0.0058 |
| 40.5 | 0.2358 | 0.2333 | 1.011 | 0.0057 |
| 41.5 | 0.2325 | 0.2300 | 1.011 | 0.0056 |
| 42.5 | 0.2293 | 0.2269 | 1.010 | 0.0056 |
| 43.5 | 0.2262 | 0.2240 | 1.010 | 0.0055 |
| 44.5 | 0.2232 | 0.2212 | 1.009 | 0.0054 |
| 45.5 | 0.2204 | 0.2186 | 1.008 | 0.0052 |
| 46.5 | 0.2178 | 0.2161 | 1.008 | 0.0051 |
| 47.5 | 0.2152 | 0.2138 | 1.007 | 0.0053 |
| 48.5 | 0.2129 | 0.2116 | 1.006 | 0.0054 |
| 49.5 | 0.2106 | 0.2094 | 1.005 | 0.0054 |
| 50.5 | 0.2085 | 0.2076 | 1.004 | 0.0054 |
| 51.5 | 0.2065 | 0.2059 | 1.003 | 0.0055 |
| 52.5 | 0.2046 | 0.2043 | 1.002 | 0.0055 |
| 53.5 | 0.2029 | 0.2028 | 1.001 | 0.0056 |
| 54.5 | 0.2013 | 0.2012 | 1.000 | 0.0056 |
| 55.5 | 0.1999 | 0.1998 | 1.001 | 0.0057 |
| 56.5 | 0.1986 | 0.1984 | 1.001 | 0.0058 |
| 57.5 | 0.1974 | 0.1970 | 1.002 | 0.0058 |

FIG. 23

| keV | $\mu/\rho$ experim. | $\mu/\rho$ theoret. | Ratio | $\sigma_{(\mu/\rho)}$ |
|---|---|---|---|---|
| 36.5 | 0.3799 | 0.3809 | 0.997 | 0.0078 |
| 37.5 | 0.3668 | 0.3652 | 1.004 | 0.0075 |
| 38.5 | 0.3543 | 0.3510 | 1.010 | 0.0073 |
| 39.5 | 0.3424 | 0.3380 | 1.013 | 0.0072 |
| 40.5 | 0.3311 | 0.3268 | 1.013 | 0.0071 |
| 41.5 | 0.3205 | 0.3169 | 1.011 | 0.0069 |
| 42.5 | 0.3104 | 0.3078 | 1.009 | 0.0069 |
| 43.5 | 0.3010 | 0.2993 | 1.006 | 0.0067 |
| 44.5 | 0.2922 | 0.2915 | 1.002 | 0.0065 |
| 45.5 | 0.2840 | 0.2842 | 0.999 | 0.0063 |
| 46.5 | 0.2764 | 0.2774 | 0.996 | 0.0064 |
| 47.5 | 0.2694 | 0.2711 | 0.994 | 0.0066 |
| 48.5 | 0.2631 | 0.2652 | 0.992 | 0.0066 |
| 49.5 | 0.2573 | 0.2598 | 0.990 | 0.0067 |
| 50.5 | 0.2522 | 0.2549 | 0.989 | 0.0067 |
| 51.5 | 0.2476 | 0.2505 | 0.988 | 0.0067 |
| 52.5 | 0.2437 | 0.2464 | 0.989 | 0.0068 |
| 53.5 | 0.2404 | 0.2424 | 0.992 | 0.0068 |
| 54.5 | 0.2377 | 0.2387 | 0.996 | 0.0069 |
| 55.5 | 0.2357 | 0.2351 | 1.002 | 0.0070 |
| 56.5 | 0.2342 | 0.2318 | 1.010 | 0.0070 |
| 57.5 | 0.2333 | 0.2286 | 1.021 | 0.0065 |

FIG. 26

| True values       | 25.225    | 19.915    | 23.783    | 20.999    | 14.605    |
|-------------------|-----------|-----------|-----------|-----------|-----------|
| Energy intervals  | Phantom 1 | Phantom 2 | Phantom 3 | Phantom 4 | Phantom 5 |
| 1                 | 25.870    | 20.041    | 24.412    | 21.349    | 14.794    |
| 2                 | 25.225    | 19.738    | 23.581    | 20.908    | 14.401    |
| 3                 | 25.944    | 19.930    | 24.691    | 21.371    | 14.897    |
| 4                 | 25.825    | 20.074    | 24.281    | 21.322    | 14.738    |
| 5                 | 25.048    | 19.966    | 24.837    | 21.432    | 14.957    |
| 6                 | 26.066    | 19.969    | 24.867    | 21.443    | 14.971    |
| 7                 | 26.034    | 19.965    | 24.815    | 21.426    | 14.949    |
| 8                 | 26.046    | 19.964    | 24.836    | 21.431    | 14.958    |
| 9                 | 26.006    | 19.959    | 23.783    | 21.407    | 14.928    |
| 10                | 26.117    | 19.963    | 24.972    | 21.471    | 15.013    |
| Average       | 25.818| 19.957| 24.507| 21.356| 14.861|

FIG. 38

| True values | 21.240 | 15.930 | 15.930 | 15.930 | 10.620 |
|---|---|---|---|---|---|
| Energy intervals | Phantom 1 | Phantom 2 | Phantom 3 | Phantom 4 | Phantom 5 |
| 1 | 21.679 | 16.013 | 16.307 | 16.183 | 10.681 |
| 2 | 21.139 | 15.791 | 15.752 | 15.765 | 10.541 |
| 3 | 21.741 | 15.924 | 16.494 | 16.200 | 10.756 |
| 4 | 21.641 | 16.039 | 16.220 | 16.163 | 10.641 |
| 5 | 21.828 | 15.953 | 16.591 | 16.246 | 10.800 |
| 6 | 21.843 | 15.956 | 16.612 | 16.254 | 10.809 |
| 7 | 21.817 | 15.952 | 16.576 | 16.241 | 10.794 |
| 8 | 21.826 | 15.951 | 16.591 | 16.245 | 10.800 |
| 9 | 21.793 | 15.947 | 16.545 | 16.226 | 10.778 |
| 10 | 21.887 | 15.950 | 16.681 | 16.275 | 10.839 |
| Average | 21.719 | 15.948 | 16.437 | 16.180 | 10.744 |

FIG. 39

| True values | 2.901 | 2.901 | 6.769 | 2.901 | 2.901 |
|---|---|---|---|---|---|
| Energy intervals | Phantom 1 | Phantom 2 | Phantom 3 | Phantom 4 | Phantom 5 |
| 1 | 3.104 | 3.026 | 7.080 | 3.053 | 3.092 |
| 2 | 3.027 | 2.783 | 6.626 | 2.906 | 2.736 |
| 3 | 3.113 | 3.009 | 7.161 | 3.056 | 3.114 |
| 4 | 3.099 | 3.031 | 7.042 | 3.049 | 3.080 |
| 5 | 3.126 | 3.015 | 7.203 | 3.065 | 3.126 |
| 6 | 3.128 | 3.015 | 7.212 | 3.066 | 3.129 |
| 7 | 3.124 | 3.015 | 7.196 | 3.064 | 3.124 |
| 8 | 3.125 | 3.015 | 7.203 | 3.065 | 3.126 |
| 9 | 3.121 | 3.014 | 7.183 | 3.061 | 3.120 |
| 10 | 3.134 | 3.014 | 7.242 | 3.070 | 3.138 |
| Average | 3.110 | 2.994 | 7.115 | 3.046 | 3.079 |

FIG. 40

| True values | 1.084 | 1.084 | 1.084 | 2.168 | 1.084 |
|---|---|---|---|---|---|
| Energy intervals | Phantom 1 | Phantom 2 | Phantom 3 | Phantom 4 | Phantom 5 |
| 1 | 1.087 | 1.002 | 1.025 | 2.114 | 1.021 |
| 2 | 1.059 | 1.165 | 1.203 | 2.237 | 1.123 |
| 3 | 1.090 | 0.997 | 1.037 | 2.116 | 1.028 |
| 4 | 1.085 | 1.004 | 1.020 | 2.111 | 1.017 |
| 5 | 1.094 | 0.998 | 1.043 | 2.122 | 1.032 |
| 6 | 1.095 | 0.998 | 1.044 | 2.123 | 1.033 |
| 7 | 1.093 | 0.998 | 1.042 | 2.121 | 1.032 |
| 8 | 1.094 | 0.998 | 1.043 | 2.122 | 1.032 |
| 9 | 1.092 | 0.998 | 1.040 | 2.119 | 1.030 |
| 10 | 1.097 | 0.998 | 1.049 | 2.126 | 1.036 |
| Average | 1.089 | 1.016 | 1.055 | 2.131 | 1.038 |

FIG. 41

THREE COMPONENT X-RAY BONE DENSITOMETRY

CROSS-REFERENCE TO RELATED APPLICATION

The benefit of U.S. Provisional Patent Application Ser. No. 60/428,300, filed Nov. 22, 2002, is hereby claimed, and the specification thereof incorporated herein in its entirety by this reference.

BACKGROUND OF THE INVENTION

"Osteoporosis is a systemic skeletal disease characterized by low bone mass and macroarchitectural deterioration of bone tissue, which leads to bone fragility and susceptibility of fracture" (Blake, et al., "The evaluation of osteoporosis: dual energy x-ray absorptiometry and ultrasound in clinical practice." Martin Dunitz Ltd 1999.). According to the National Osteoporosis Foundation one in two women and one in eight men over the age of fifty will have an osteoporotic-related fracture in their lifetime. Eight million American women and two million men have osteoporosis and millions more have low bone density. The use of noninvasive bone densitometry has resulted in significant improvement in the early detection of osteoporosis.

Dual x-ray absorptiometry (DXA) is the most often used method in the measurement of bone mineral density because of the low cost, low radiation dose and the possibility of measurement at the anatomical site where the fractures most commonly occur (femur, spine). (See Genant, et al., "Noninvasive assessment of bone mineral and structure: state of the art." *J Bone Miner Res*. 11: 707–30 (1996)). By using only two energies, the dual x-ray absorptiometry method is limited to distinguishing tissue composition to two components (muscle and bone or muscle and adipose tissue). To correct for different tissue composition (varying proportions of lean and adipose tissue), the fat fraction is calculated over the soft tissue part of the patient where no bone is present. The assumption is made that adipose tissue is uniformly distributed and the soft tissue composition adjacent to the bone is the same as the soft tissue overlying the bone. However, in fact, fat is not uniformly distributed and therefore, this assumption can introduce errors of greater than 10% in a significant percentage of the patient population. (See Svendsen, et al. "Impact of soft tissue on in-vivo accuracy of bone mineral measurements in the spine, hip and forearm: a human cadaver study." *J Bone Miner Res* 10: 868–73, (1995); Tothill, et al. "Errors due to non-uniform distribution of fat in dual x-ray absorptiometry of the lumbar spine." *Br J Radiol* 65:807–13, (1992); Farrell, et al. "The error due to fat inhomogenity in lumbar spine bone mineral measurements." *Clin. Phys. Physiol. Meas.* 10 57–64, (1989)).

It would be desirable to provide a method and apparatus that can, from the energy distribution of the x-ray spectra, incident and transmitted through the patient, determine the areal densities of the three tissue components: bone, fat and soft tissue. The present invention addresses this need and others in the following manner.

SUMMARY

The present invention relates to deriving the in vivo three-component areal density composition of a patient along a transmitted x-ray beam by raster-scanning a collimated x-ray beam across a bony region of the patient, deriving the x-ray energy spectrum at each point, and using matrix equations with a priori spectra information to solve for the relative areal density of soft tissue, fat and bone.

It is to be understood that both the foregoing general description and the following detailed description are exemplary and explanatory only and are not restrictive of the invention, as claimed.

BRIEF DESCRIPTION OF THE DRAWINGS

The accompanying drawings illustrate one or more embodiments of the invention and, together with the written description, serve to explain the principles of the invention. Wherever possible, the same reference numbers are used throughout the drawings to refer to the same or like elements of an embodiment, and wherein:

FIG. 6 is an excerpt of computer code illustrating an iterative process that takes the sum of the individual solutions and estimates the areal density of the individual components.

FIG. 7 shows the composition and fraction by weight of the constituent elements provided by the manufacturer for the three types of tissue used in the study.

FIG. 10 shows values of areal densities and the compositions of the phantoms.

FIG. 14 shows the mean values of number of photons, standard deviations and coefficients of variation of the ten x-ray spectra illustrated in FIG. #13.

FIG. 16 shows the mean values of number of photons, standard deviations and the coefficients of variation of the x-ray spectra shown in FIG. #15.

FIG. 20 shows a comparison of experimentally and theoretically derived mass attenuation coefficients of the muscle simulating phantom.

FIG. 23 shows a comparison of experimentally and theoretically derived mass attenuation coefficients of the adipose tissue simulating phantom.

FIG. 26 shows a comparison of the experimental and theoretically derived mass attenuation coefficients of the bone tissue simulating phantom.

FIG. 38 is a table showing the sum of areal densities of the phantoms calculated using Cramer's method.

FIG. 39 is a table showing calculated values of muscle areal densities.

FIG. 40 is a table showing calculated values of adipose tissue areal densities.

FIG. 41 is a table showing calculated values of bone areal densities.

DETAILED DESCRIPTION

Figure 1:
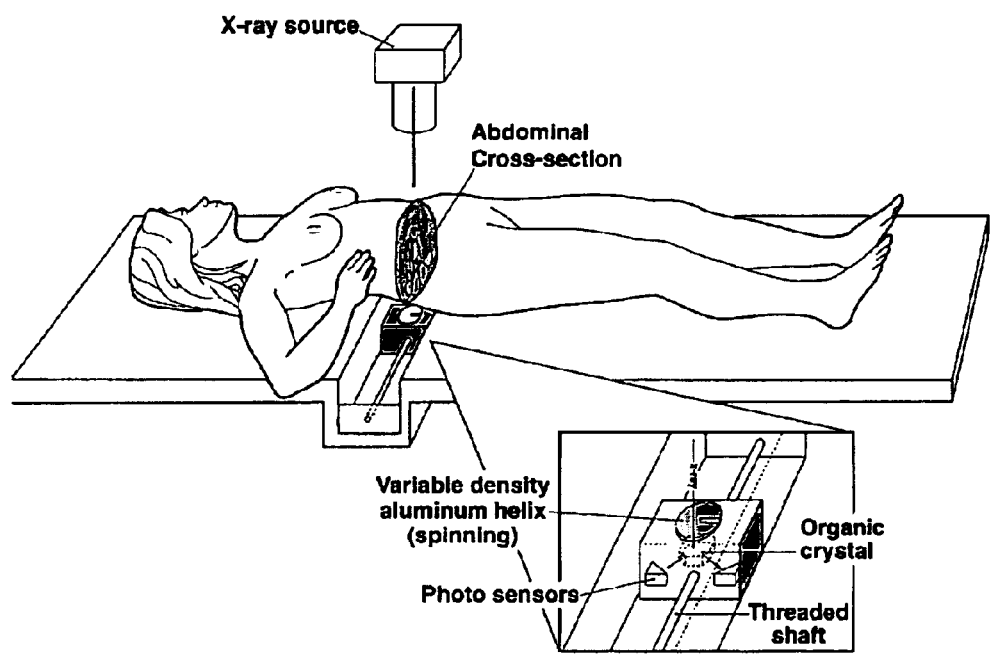
FIG. 1 illustrates an apparatus for determining areal densities of bone, fat and soft tissue in a patient.

The present invention relates to a system and method for determining areal densities of bone, fat and muscle in a localized area of a patient. As illustrated in FIG. 1, an apparatus can be used that includes a couch on which a patient lies, a scanning x-ray source and detector system and a computing system (not shown for purposes of clarity). Stored in or otherwise accessible to the computing system is a database or other collection of spectral curves that have been predetermined for the apparatus by experimental measurement, as described below.

The coordinate system used in the following idea is rectangular and has +Y at the head of the patient lying supinely on a couch and −Y at the foot of the patient. +X corresponds to the left side of the patient and −X corresponds to the right side of the patient. +Z is in the direction of the x-ray source above the patient and −Z is in the direction of the x-ray beam.

Figure 42:
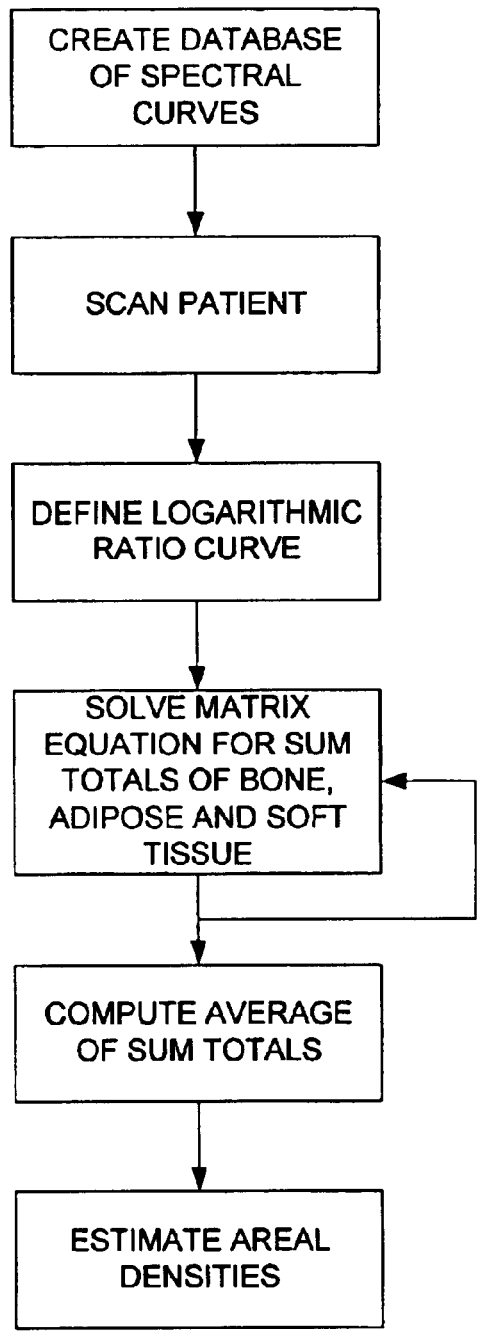
FIG. 42 is a flow diagram illustrating a method for determining areal densities of bone, fat and soft tissue in a patient.

The following method for determining areal densities of bone, fat and muscle in a localized area of a patient follows the flow diagram of FIG. 42. After the database of curves has been created and stored as described below, the apparatus scans a localized area of a patient in a raster fashion, with the computer collecting data representing the measured intensity of the collimated x-ray beam after having passed through the patient at many points. At each point, the intensity of the beam is measured at a number of different filter thickness values interposed in the beam. An x-ray energy transmission curve is then computed from the collected intensity data.

The x-ray source and detector system includes an x-ray machine fixedly coupled to an x-ray detector by a gantry (not shown in FIG. 1 for purposes of clarity), and a scanning mechanism (also not shown) that moves the gantry laterally across the supine patient in either the ±x direction and then increments in the ±Y direction in a raster fashion. In this fashion, a collimated beam of x-rays is moved across a defined region of the patient that contains a bony structure.

Suitable x-ray machines include those that can run continuously for several minutes in a kilovoltage range from approximately 40–50 kVp for infants and small children to 120–140 kVp for large and obese adults. The x-ray machine should be able to deliver up to 3,000 watts of electrical power, e.g., 20 mA at 140 kVp, for several minutes, e.g., 5–20 minutes. The x-ray beam is collimated to a small aperture which is aligned to hit a detector on the distal or back side of the patient.

The detector system includes a rotating filter wheel or other suitable means for varying the intensity of the x-ray beam, suitable x-ray sensors and a collimator that directs the collimated beam upon the sensors. The filter wheel can be a metal (e.g., aluminum, copper, etc.) disk having sectors of different thicknesses. The thickness can increase from sector to sector such that the disk resembles a spiral staircase.

Figure 4:
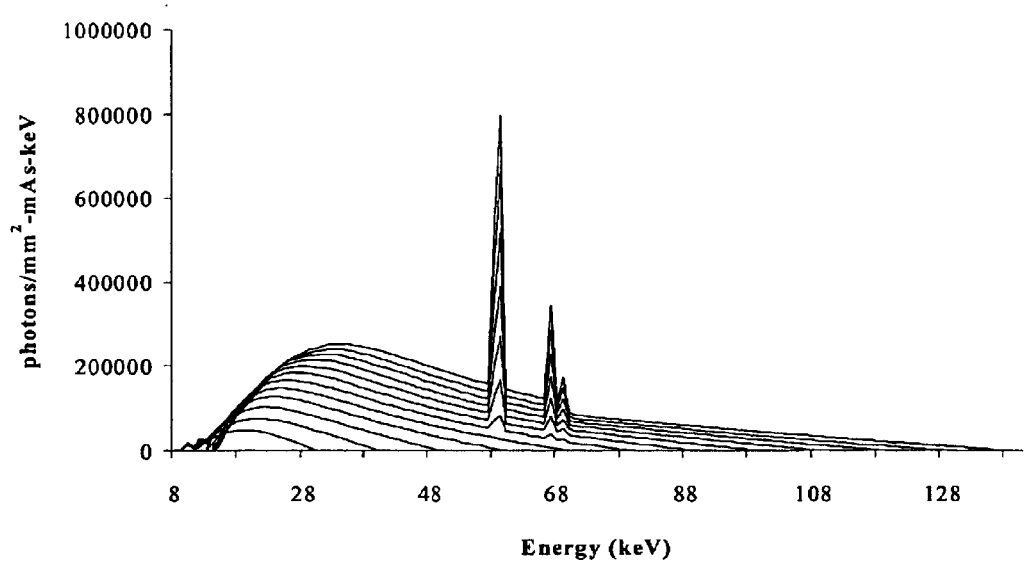
FIG. 4 shows 11 exemplary x-ray spectra from 40 kVp to 140 kVp with a 0.5 mm aluminum (Al) added filter. These spectra are drawn from the database which was constructed from measured transmission curves.

As described in further detail below, the x-ray transmission curve computed from the measured intensity data can be used to obtain a corresponding spectral curve, examples of which are shown in FIG. 4. In the spectral curves, the number of x-ray photons (or spectrophotometer counts) at each energy present in the spectrum is plotted against the energy in keV.

Figure 2:
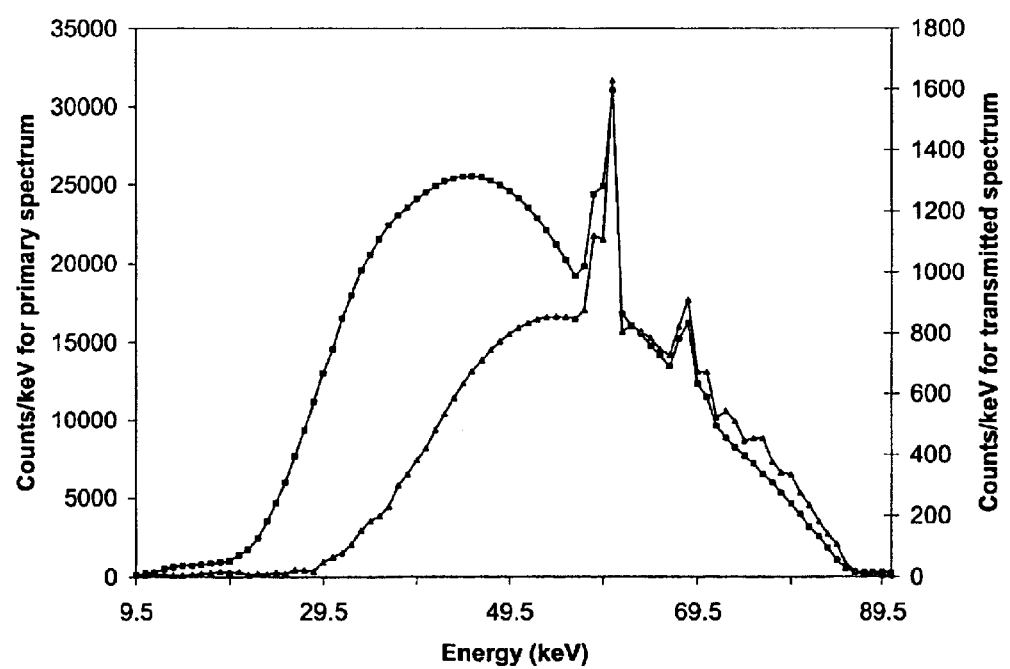
FIG. 2 shows some exemplary curves from an extensive database of measured spectral curves for in-air, i.e., unattenuated, x-ray beam and an x-ray beam attenuated by a phantom simulating body composition of bone, muscle and fat.

As noted above, an extensive database of pre-computed or predetermined spectral curves, which may resemble the curves shown in FIG. 4, is accessible to the computer. These spectral curves or spectra have been pre-computed using a laboratory spectrometer in the system without a patient in place on the couch. In other words, the curves in the database describe the spectra of in-air beams, i.e., beams that pass only through air and are thus unattenuated. (The intensity of an in-air beam is referred to as Io in the equations described below.) The upper curve in FIG. 2 illustrates the x-ray energy spectra for an in-air x-ray beam, and the lower curve illustrates the same spectrum after it has passed through the patient and has been attenuated.

The computed x-ray spectra are stored in the database as a function of kVp and added filter. The added filters used in pre-computing the spectra need not be the spinning disk filter described above that is used when the system is actually in use with a patient. Rather, the added filters used in this pre-computing step can be variable filters of made of a suitable material. The variable filters can be composed of metal of different thicknesses or can be composed of different thicknesses of bone mineral, fat, and soft tissue.

FIG. 4 shows 11 x-ray spectra from 40 kVp to 140 kVp with 0.5 mm aluminum (Al) added filter. FIG. 4 is intended merely to illustrate a number of spectra of the type that may be stored in the database; the database can actually include any of several thousand x-ray spectra.

Figure 5:
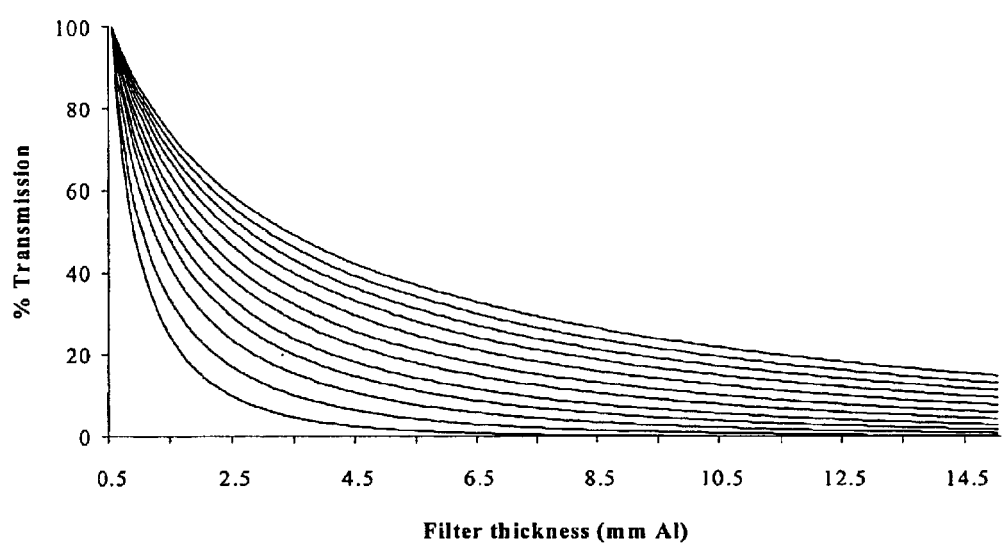
FIG. 5 shows transmission (attenuation) curves of each of the spectra shown in FIG. 4 using an added aluminum (Al) filter.

As noted above, a transmission curve computed from the measured intensity data can be used to obtain a corresponding spectral curve. FIG. 5 illustrates this correspondence by showing transmission (attenuation) curves of each of the spectra shown in FIG. 4 using an added aluminum (Al) filter. Note that this curve has a distinctive shape for each kVp.

The upper range of added aluminum filter thickness in this example is 15 mm or 1.5 cm, but Al filter thicknesses of up several centimeters may be suitable. The typical adult body will have an attenuation corresponding to around 20 mm Al or two cm Al. The curve-matching process can thus start at around 15 to 20 mm Al.

The database of spectral curves is searched until one is found that substantially matches the transmission curve defined by the collected data. As known in the art, an x-ray spectral curve relates beam energy to beam intensity at each beam energy. The bone density determination process can be started for any particular patient with a knowledge of the Io (e.g., the upper x-ray spectrum in FIG. 2) as it is stored in the database and is determined from the kVp and added filter applied to the x-ray unit.

As described above, when the system is in use on a patient, measurements are obtained with a spinning wheel Al filter of different thickness below the patient. Suppose the x-ray source is running at 140 kVp. A measured curve through 5.5 mm Al can be matched to the pre-computed curve for 140 kVp as a function of the filter by sliding it down the 140 kVp curve until it matches the original curve beginning at 6 mm Al and extending to 11.5 mm Al. This indicates that the patient or phantom at that point had an equivalent thickness of 6 mm Al. From this value, the computer looks up in the database the x-ray spectra at 140 kVp corresponding to 6 mm Al thickness and uses that for the lower x-ray spectrum in FIG. 2. The computer then derives or reads from the database the x-ray spectrum from the group of x-ray spectra as shown in FIG. 4 that is unique for that patient thickness and composition of soft tissue, fat and bone, at that kVp and added filter which enables the operations as described below.

From the spectral curve found in the database, a curve is computed that relates the logarithm of the ratio of beam intensity in air divided by the measured beam intensity after passing through the patient to each of a plurality of photon energies in the beam. In other words, the computer is able to derive a spectrum such as the lower curve shown in FIG. 2 and then calculate a curve such as that shown in FIG. 3 below by knowing the original intensity at any photon energy Io(E) from the measurements and calculations we have already performed in the laboratory for that particular unit. Then, the computer computes the intensity I(E) of the transmitted x-ray intensity through the patient for each photon energy. From the spectra, both transmission and unattenuated, the curve can be derived from $\log[Io(E)/I(E)]$ as shown in FIG. #3.

In the next step of the method, which is described in further detail below, the computer solves a matrix equation for the sum totals of the areal densities of bone, fat and muscle in response to predetermined mass attenuation coefficients for bone, fat and muscle at a group of three selected energies and in response to the logarithmic ratio obtained from the curve at each of the three selected energies. There are three energies in the group because that is the number needed for the matrix equation to determine three areal densities (bone, fat and muscle). The matrix equation is solved many times, each at a different group of three selected energies.

Before the details of this step are described, it should be noted that the basis for determining the muscle, fat and bone mineral components at any x-y point or pixel is the following equation, which is well-known to persons skilled in the art to which the invention relates:

$$I(X,Y) = I_0(X,Y)\exp(-\mu_s X_s - \mu_f X_f - \mu_b X_b) \tag{1}$$

$Io(X,Y)$ is the x-ray intensity in air at the point or without a patient in place, $I(X,Y)$ is the x-ray intensity in air with the patient in place, $\mu_{s,f,b}$ are the mass attenuation coefficients for muscle, fat and bone respectively, and $X_{s,f,b}$ are the products of physical densities and thickness of muscle, fat and bone, respectively transverse by the photons beam.

First, the following quantity is computed at each energy Ei in the x-ray spectra:

$$\ln\left(\frac{I_{0i}}{I_i}\right) = \mu_{bi}X_b + \mu_{si}X_s + \mu_{fi}X_f \quad (2)$$

For the exemplary x-ray spectra shown in FIG. 2, this energy range is 36.5 to 57.5 keV. An exemplary curve described by this quantity at a number of energies Ei is shown plotted in FIG. 3. The curve is the starting point for the mathematical solution to obtain the three component values.

Figure 3:
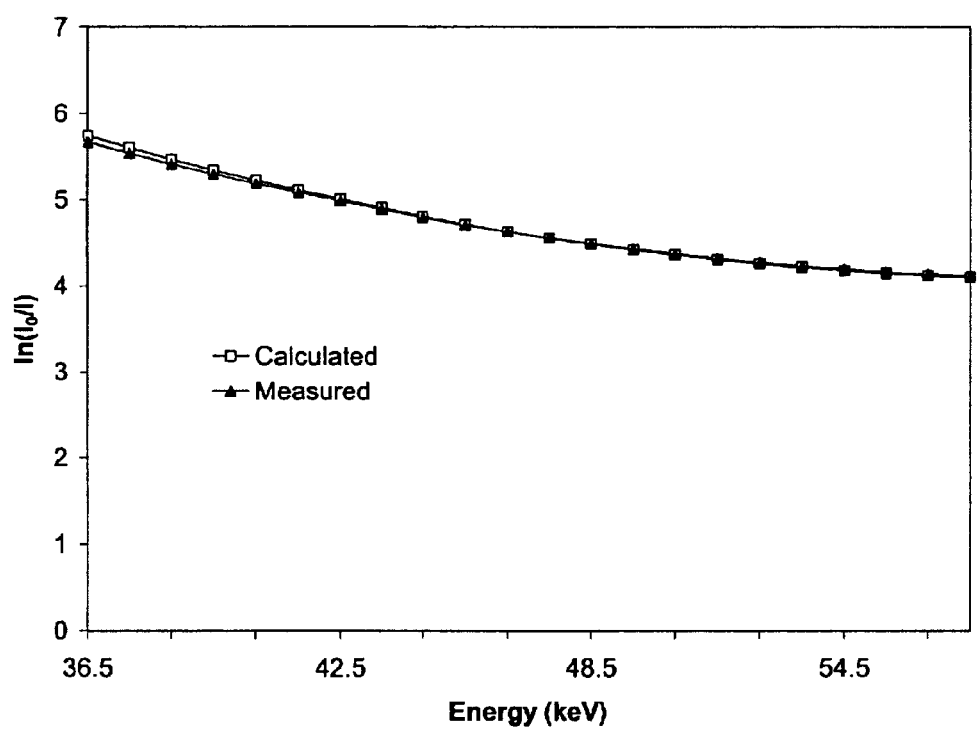
FIG. 3 shows exemplary curves of the logarithm of the ratio (Io/I) at the photon energy range, 36.5 to 56.5 keV derived from x-ray spectra similar to those shown in FIG. #2 for both calculated and measured x-ray spectra.

The exemplary curve shown in FIG. 3 was obtained from 22 computations of Equation 2, but any suitable number of computations can be used. Note that in this example as many as 1,540 unique groups of three energy values along this curve can be selected to solve for the areal density of muscle, fat and bone mineral. (The number of permutations of three values selected from 22 values is 1,540.) It is believed suitable to use only 22 equations, with the values of photon energies separated by some optimal energy spacing.

Three separate energies are arbitrarily selected from n energy intervals of the x-ray spectrum. Assuming narrow beam geometry, and that the object has three components, the three attenuation equations can be written for these energy intervals as:

$$I_1 = I_{01}\exp(-\mu_{b1}X_b - \mu_{s1}X_s - \mu_{f1}X_f)$$
$$I_2 = I_{02}\exp(-\mu_{b2}X_b - \mu_{s2}X_s - \mu_{f2}X_f)$$
$$I_3 = I_{03}\exp(-\mu_{b3}X_b - \mu_{s3}X_s - \mu_{f3}X_f) \quad (3)$$

where: $I_{0(1,2,3)}$ is the unattenuated intensity of the energy interval 1, 2 and 3, $I_{(1,2,3)}$ is the transmitted intensity in the energy interval 1, 2 and 3. The coefficients, $\mu_{s,f,b}$, are the mass attenuation coefficients in cm$^2$/g of each component whose surface densities are X in g/cm$^2$, and b, s, f are indices for bone, soft tissue and fat respectively. The equations can be written in matrix notation as:

$$\begin{bmatrix} \mu_{b1} & \mu_{s1} & \mu_{f1} \\ \mu_{b2} & \mu_{s2} & \mu_{f2} \\ \mu_{b3} & \mu_{s3} & \mu_{f3} \end{bmatrix} \times \begin{bmatrix} X_b \\ X_s \\ X_f \end{bmatrix} = \begin{bmatrix} \ln(I_{01}/I_1) \\ \ln(I_{02}/I_2) \\ \ln(I_{03}/I_3) \end{bmatrix} \quad (4)$$

or in the simpler form $$A \times X = B \quad (5)$$

and the solution can be obtained using the inverse $[\mu]^{-1}{}_i$ $$\begin{bmatrix} X_b \\ X_s \\ X_f \end{bmatrix} = \begin{bmatrix} \mu_{b1} & \mu_{s1} & \mu_{f1} \\ \mu_{b2} & \mu_{s2} & \mu_{f2} \\ \mu_{b3} & \mu_{s3} & \mu_{f3} \end{bmatrix}^{-1} \times \begin{bmatrix} \ln(I_{01}/I_1) \\ \ln(I_{02}/I_2) \\ \ln(I_{03}/I_3) \end{bmatrix} \quad (6)$$

The linear equation contains three unknowns: $X_b$, $X_s$, and $X_f$. Several mathematical methods have been applied to solve such a linear equation.

The determinant of matrix A in Equations 4 and 5 above has a very small value. This makes it very difficult to solve as it is ill conditioned. If perfect input data were put into matrix B then a perfect solution would be obtained, but this is not possible for any kind of measured data. The individual values of the components obtained by this method will vary widely for each solution and they will range from large negative values to large positive values for the different components. These values make no physical sense in many cases. By studying the solutions, it was discovered in accordance with the present invention that even though the individual solutions were not correct, the sum of the individual solutions for the three components was almost correct. ("Almost correct" in the sense that it varied at most only a few percent or always less than 5% from the known correct sum solution for phantoms that were measured in the laboratory.) The novel method of the present invention for determining the three components is based upon this discovery. For example, two of the values can be negative and one can be positive, but it was discovered that their sum would be very close to the correct and true sum. This was determined from phantom measurements with accurately known chemical compositions.

The computer, operating in accordance with suitable programming to effect the method described herein, takes the sum of the individual solutions and estimates the areal density of the individual components. The starting point for this process is patient parameter-dependent. For example, a first estimate can be made for the fraction of muscle, fat and bone mineral along a ray which is dependent upon the patient's sex, age, level of obesity and exogenous factors such as known osteoporosis, diseases, etc. An exemplary software code excerpt illustrating the iterative process is shown in FIG. 6. In the code, Kg1 represents the estimated fraction of total areal density for muscle, Kg2 represents the estimated fraction of areal density for fat or adipose tissue, kg3 represents the estimated fraction for bone, sumrhoxg denotes the average sum of the different determinant or matrix solutions or correct value, p5 denotes a particular phantom or patient, and 1,2,3 in the array denote soft tissue, fat and bone, respectively. Sumdifbest is initialized to a large value to start the loop. The loop iterates to determine the best fraction of total areal density for soft tissue, fat and bone. Conceptually, on each iteration, the computer is generating a curve in response to estimates of areal densities of bone, fat and muscle and then comparing the generated curve to the logarithmic curve until a match within predetermined threshold limits is identified. Persons skilled in the art to which the invention relates will readily be capable of providing a computer with suitable programming to effect the above-described steps.

As in dual x-ray bone densitometry, the x-ray beam has passed through a thickness of tissue adjacent to a bone structure where the x-ray beam does not actually encounter any bone structures, i.e. right adjacent to the spine in the body below the diaphragm and above the pelvis. In such a case, there are only two components: soft tissue and fat. If the transmitted x-ray spectrum is known at this point, the low and high energy can be selected from the x-ray spectrum and solved to obtain the area density of soft tissue as in dual x-ray absorptiometry as:

$$X_s = \frac{\ln(I_{0L}/I_L) - [\ln(I_{0H}/I_H)]\mu_{fL}/\mu_{fH}}{\mu_{sL} - \mu_{fL}\mu_{sH}/\mu_{fH}} \quad (7)$$

The subscripts L and H correspond to lower and higher photon energies.

Similar equation can be written for areal density of adipose tissue.

As the scanning x-ray beam passes into the region containing bone, the solution values for muscle and fat outside the bone can be taken and subtracted from the sum values with bone included to obtain a first estimate for the bone mineral values. The values of areal density obtained for each component are passed into a an iteration routine whereby the type of curve shown in FIG. 3 is calculated and compared to a measured such as the measured curve shown in FIG. 3 curve. The sum of the absolute difference at point by point energy comparison is calculated. Then, in an iterative fashion, the measured fractional areal densities of the different components can be varied slightly in both the plus and minus directions and a new curve is calculated. If the sum of the absolute difference of this curve is greater than the previous absolute difference, the areal densities can be perturbed in the opposite direction. In this fashion, each fractional areal density can be perturbed to finally obtain those fractional values of the areal density that yield the least sum of the absolute difference, energy point by energy point, of the calculated and measured curves.

In cases in which values for muscle and fat cannot be obtained, i.e. the beam does not go through a bone-free region adjacent to bone, a number of matrix solutions (e.g., from 1 to several thousand) can be computed and an average value of their sum computed.

While the description set forth above is believed sufficient to enable persons skilled in the art to which the invention relates to make and use the invention, the following discussion of the theoretical and practical underpinnings of the invention may be of interest to the reader.

A specific underpinning of the invention involved a study with experiments in which the x-ray spectra incident and transmitted through a phantom simulating tissue were measured using a semiconductor detector and multichannel analyzer (not shown). The measured spectra were used to calculate the mass attenuation coefficients of the phantoms simulating tissue as a function of energy and compare them with theoretically derived values.

Another specific underpinning of the invention involved experiments in which the x-ray spectra incident and transmitted through the multiple tissue simulating compositions was measured. Spectra were obtained for a variety of phantom compositions. The fractional logarithmic transmissions were calculated for each phantom and compared with the sum of the products of mass attenuation coefficients and areal densities of the phantom components.

Still another specific underpinning of the invention involved developing a computer program to calculate the areal densities of the phantom components (muscle, bone, adipose tissue) from the measured spectra.

The spectroscopy system used in these studies (not shown) employed a planar, low energy, high purity germanium (LEGe) detector cooled in liquid nitrogen, Canberra model GL0510. The detector had an active area of 500 mm², diameter of 25.2 mm and a thickness of 10 mm. The detector was equipped with a 0.15 mm beryllium (Be) window and the distance from the beryllium window to the germanium crystal was 5 mm. The bias voltage of the detector was 1500 volts. The preamplifier was built into the detector assembly. The spectroscopy system used a Canberra amplifier model 2022 and a Canberra high voltage supply model 1000. The output from the amplifier was connected to the multichannel analyzer, such as an Ortec-Norland 5600 model having a 100 MHz ADC.

The energy calibration of the multichannel analyzer was performed by exposing the detector to known energies of Co-57 (14.41 keV), Am-241 (59.536 keV) and Ba-133 (80.99 keV) sources. The photopeaks were centered in the energy channel using the built in multichannel analyzer function. The conversion gain of the multichannel analyzer was set to 1024 and the amplifier was set to display 1 keV per channel, i.e. channel 20 measured photons from 19 to 20 keV. The linearity of the multichannel analyzer (the relationship between gamma-ray energy and multichannel analyzer channel number) was measured with the same sources as used for the energy calibration.

The data acquired in this study was measured using a constant potential dental x-ray unit (not shown), Keystone model 2497-100Y, equipped with a cone. The system operated in the 60–90 kVp range with tube currents of 0.01 mA to 1 mA. There is a very small ripple associated with the constant potential output (<3%). The unit employs a thick tungsten target with an anode target angle of 15 degrees. The beam is modified by 3 mm aluminum total filtration (1 mm inherent and 2 mm added). The kVp and tube current are displayed during the exposure at the control panel. During the data collection, the x-ray target-detector distance was 130 cm. To reduce the primary photon fluence rate, the x-ray beam was collimated in three different steps. The source was equipped with a lead collimator with a diameter of 15 mm and thickness of 40 mm. A lead collimator with an aperture diameter of 1 mm and lead thickness of 5 mm plus 2 mm of aluminum was used at the detector so that photon penetration through the collimator wall was negligible for operating tube potentials. Additionally, a lead collimator with the diameter 2 mm and thickness of 65 mm was positioned 66 cm from the target.

An important element in this study was the stable and reproducible energy spectrum of the x-ray unit. To achieve a sufficient number of photons without overheating the x-ray unit, the exposure time was set at 50 seconds. The multichannel analyzer operated in the "add all" mode and added photons emitted in the successive exposures. To check for the reproducibility of x-ray spectrum, ten exposures of 50 seconds duration were taken at 85 kVp and 0.01 mA current. These are the x-ray spectra shown in FIG. 13. To reduce the dead time, the spectrum was measured with 7.0 cm of acrylic in the beam. The dead time as displayed by the multichannel analyzer was 0–1%. The reproducibility was obtained by calculating coefficients of variation for the selected energy channels. The standard deviation of the ten 50 second exposure spectra was calculated from the formula:

$$SD_I = \frac{\sqrt{\sum_{i=1}^{10} I_i}}{N} \tag{8}$$

Where: $SD_I$ is the standard deviation of the mean value; $I_i$ is the observed number of counts in the selected energy interval and N is the number of exposures. The coefficient of deviation for the selected energy intervals is:

$$CV = \frac{SD_I}{\bar{I}} \tag{9}$$

As mentioned above, for the measurements of the mass attenuation coefficient as well as the bone mineral measurements, the photons collected for several 50 second exposures were added. The standard deviation of the mean and coefficient of variation for six 500 seconds exposures (which is the sum of ten 50 seconds exposures) at each photon energy were also calculated.

Tissue simulating phantoms were manufactured by Computerized Imaging Reference Systems, Inc. FIG. 7 shows the composition and fraction by weight of the constituent elements provided by the manufacturer for the three types of tissue used in this study. The mass attenuation coefficients of the tissue simulating material components was taken from Hubbell and Seltzer and interpolated at 1 keV intervals using the Newton interpolation divided difference formula. (See Hubbell, et al. "Tables of X-ray mass attenuation coefficients and mass energy absorption coefficients 1 keV to 20 MeV for elements z=1 to 92 and 48 additional substances of dosimetric interest." NIST, 1995.) The table values were derived at mid-channel values, i.e. 19.5 keV for channel 20. The values of the mass attenuation coefficients of the tissue simulating components were calculated by adding the values of the mass attenuation coefficients of the elements according to their proportions by weight.

$$\frac{\mu}{\rho}(E) = \sum_i w_i \left(\frac{\mu}{\rho}(E)\right)_i \tag{10}$$

where: $w_i$ is the fraction by weight of the i-th element and $(\mu/\rho)_i$ are the interpolated values of atomic element of the mass attenuation coefficients at the photon energy E.

The table of FIG. 7 shows the densities and fractional composition by weight of tissues included in the measurements.

The response function of the spectrometer is the analyzer pulse height distribution. To obtain an accurate determination of the incident photon spectrum, the measured pulse height distribution needs to be corrected for detector distortion. The measured values used in the experiment are the pulse height distribution not corrected for detector characteristics. This was based on assumption, that both primary and transmitted spectra were distorted in the same way by the measurements. The distortion will cancel out in both denominator and numerator. We believe that this assumption is correct if both measurements were made with the same dead time.

The materials simulating the muscle, adipose tissue and bone were placed behind the middle collimator, 66 cm away from the tube target. To achieve the same dead time as displayed on multichannel analyzer all measurements were taken with 7 cm of acrylic in the primary beam. The acrylic was placed behind the middle collimator. The transmitted beam was measured by placing the tissue simulating materials behind the acrylic. Exposures of 500 seconds duration were taken for both the primary and transmitted spectra. For all measurements, the dead time, as displayed on the multichannel analyzer, was 0–1%. The mass attenuation coefficients were calculated knowing the overall thickness and physical density of the tissue from the attenuation equation:

$$\frac{\mu}{\rho} = \frac{\ln(I_0/I)}{\rho x} \tag{11}$$

where: $I_0$ is the number of photons measured in the energy channel with only the acrylic in the beam and I is the number of photons measured with acrylic and muscle, adipose, or bone simulating phantoms. $\rho$ is the physical density, in g/cm$^3$, and x is the thickness of the tissue transversed by the photons, in cm. The measured mass attenuation coefficients were fitted to a second order polynomial.

Assuming a perfect detector, negligible error in the thickness measurement and ignoring any effect due to scatter radiation, the uncertainty associated with the measurement of the mass attenuation coefficients was calculated using propagation of errors from the formula:

$$\sigma_{(\frac{\mu}{\rho})} = \sqrt{\frac{1}{\rho^2 x^2}\left(\frac{1}{I} + \frac{1}{I_0}\right)} \tag{12}$$

where: $\sigma_{(\mu/\rho)}$ is the standard deviation, $\rho$ is the physical density of the material being measured, $I_0$ is number of counts per channel for the primary beam and I is the number of counts for the transmitted beam.

Figure 8:
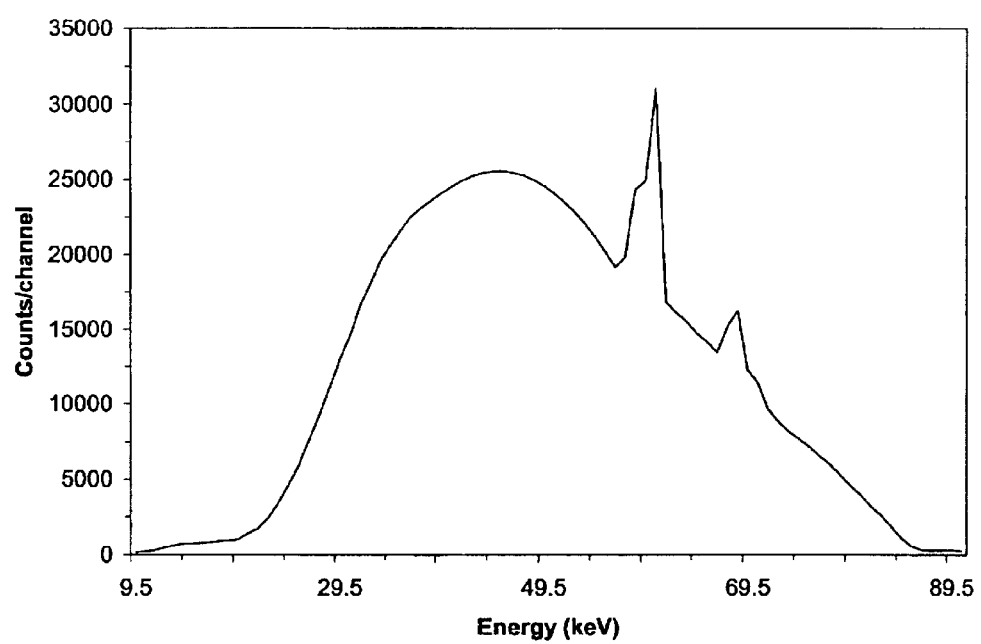
FIG. 8 shows the pulse height distribution of the photons of the primary spectrum obtained with an acrylic water container and acrylic in the x-ray beam for 87 kVp, 0.01 mA tube current and 500 second duration.
Figure 9:
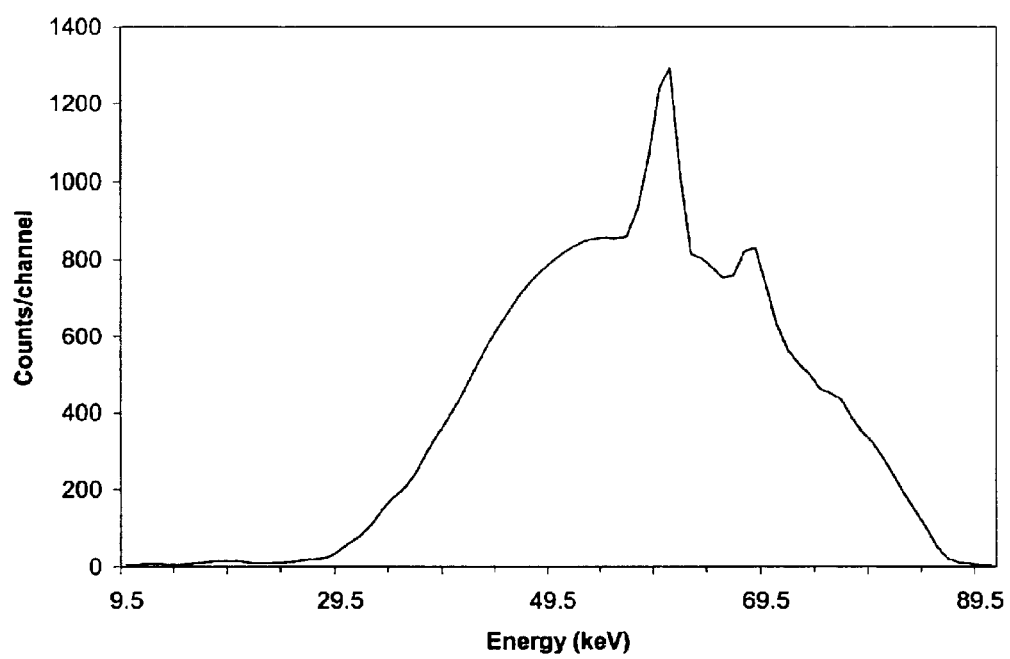
FIG. 9 shows the pulse height distribution of the photon spectrum for the container after filling the container with 15 cm of water.

The shape of the spectrum, when the x-ray beam was attenuated by 15 cm of water is shown in FIG. 9 and the primary spectrum is shown in FIG. 8. On comparison with the primary spectrum the maximum is shifted to approximately 57 keV and photons below 30 keV are almost completely absorbed. This is the reason that the data analysis was restricted to the energy range of 36.5–57.5 keV on the x-ray spectrum.

FIGS. 8 and 9 illustrate spectra used to determine the energy range of interest. FIG. 8 shows the pulse height distribution of the photons of the primary spectrum for 87 kVp, 0.01 mA tube current and 500 second duration obtained with the acrylic water container and an additional 3.2 cm of acrylic in the x-ray beam. FIG. 9 shows the pulse height distribution of the photon spectrum obtained after filling the container with 15 cm of water.

Five different phantoms were assembled from the three components simulating human tissue. The geometry consisted of stacks of three slabs with varying thickness of each of three materials with the adjacent slabs in contact with each other. In four of the phantoms, bone mineral areal densities were 1.084 g/cm$^2$. The value of about 1/cm$^2$ corresponds to the value typically encountered in the measurement of the spine and femoral neck. (See Dunn, et al., "Measurement of bone mineral content in human vertebrae and hip by dual photon absortiometry." Radiology 156, 203 (1985); Wahner, et al., "Dual-photon Gd-153 absortiometry of bone." Radiology 156, 203 (1985). Measurements of bone mineral density over a range of soft tissue compositions were made by changing the relative thickness of muscle and fat. The simulated muscle had thicknesses of 10, 15 and 20 cm. The adipose tissue mass percentage of soft tissue in the assembled phantoms ranged from 13% to 40%. These values span the normal range of fat measured in the body. (See Wang, et al., "Body fat from body density: underwater weighting vs. dual-photon absortiometry." Am. J. Physiol. 256, 1989). The composition and thickness of phantom components is shown in Table 2. To prevent saturation of the spectrometer system and keep the detector pile-up effect at a negligible level the open beam ($I_0$) was measured with the lowest tube current available (0.01 mA) and with 0.1 mm of Cu in the beam. The data obtained was corrected for the copper attenuation and the ratio of currents. Phantom measurements were obtained with higher tube currents. During the phantom measurements, the tube current varied from 0.029 mA to 0.343 mA.

By knowing the mass attenuation coefficients and areal densities of the three phantom components, the sum of the products of mass attenuation coefficients and areal densities of the phantom components can be calculated from formula 13 (right side of equation).

$$\ln\left(\frac{I_{0i}}{I_i}\right) = \mu_{bi} X_b + \mu_{si} X_s + \mu_{fi} X_f \tag{13}$$

where $I_{0i}$ corresponds to the number of photons in the primary beam at energy interval i, $I_i$ is the transmitted number of photons through the phantom at the same energy interval, $\mu_{b,s,f}$ is the mass attenuation coefficients for bone, muscle and adipose tissue, respectively, and $X_{b,s,f}$ are the areal densities of the phantoms components. The table of FIG. 10 shows the values of areal densities and the compositions of the phantoms.

From the measured spectra, the fractional logarithmic transmission (left side of the equation 13) was calculated for the energy range of 36.5–57.5 keV and compared with the sum of the products of mass attenuation coefficients and areal density of phantom components (right side of the equation 13).

Three separate energies can be randomly selected from n energy intervals of the x-ray spectrum. Assuming narrow beam geometry, and that the object has three components, three attenuation equations can be written for these energy intervals as:

$$I_1 = I_{01} \exp(-\mu_{b1} X_b - \mu_{s1} X_s - \mu_{f1} X_f)$$

$$I_2 = I_{02} \exp(-\mu_{b2} X_b - \mu_{s2} X_s - \mu_{f2} X_f)$$

$$I_3 = I_{03} \exp(-\mu_{b3} X_b - \mu_{s3} X_s - \mu_{f3} X_f) \quad (14)$$

where: $I_{0(1,2,3)}$ is the unattenuated intensity of the energy interval 1, 2 and 3, $I_{(1,2,3)}$ is the transmitted intensity in the energy interval 1, 2 and 3. The coefficients, $\mu_{s,f,b}$, are the mass attenuation coefficients in cm$^2$/g of each component whose surface densities are X in g/cm$^2$ and b, s, f are indices for bone, muscle and fat respectively.

The equations can be written in matrix notation as:

$$\begin{bmatrix} \mu_{b1} & \mu_{s1} & \mu_{f1} \\ \mu_{b2} & \mu_{s2} & \mu_{f2} \\ \mu_{b3} & \mu_{s3} & \mu_{f3} \end{bmatrix} \times \begin{bmatrix} X_b \\ X_s \\ X_f \end{bmatrix} = \begin{bmatrix} \ln(I_{01}/I_1) \\ \ln(I_{02}/I_2) \\ \ln(I_{03}/I_3) \end{bmatrix} \quad (15)$$

or in the simpler form $$A \times X = B \quad (16)$$

and the solution can be obtained using the inverse $[\mu]^{-1}$i $$\begin{bmatrix} X_b \\ X_s \\ X_f \end{bmatrix} = \begin{bmatrix} \mu_{b1} & \mu_{s1} & \mu_{f1} \\ \mu_{b2} & \mu_{s2} & \mu_{f2} \\ \mu_{b3} & \mu_{s3} & \mu_{f3} \end{bmatrix}^{-1} \times \begin{bmatrix} \ln(I_{01}/I_1) \\ \ln(I_{02}/I_2) \\ \ln(I_{03}/I_3) \end{bmatrix} \quad (17)$$

The linear equation contains three unknowns: $X_b$, $X_s$, and $X_f$. Several mathematical methods have been applied to solve this linear equation.

As previously stated, the energy range selected on the x-ray spectra for use in this project contains twenty two channels in the energy range of 36.5 to 57.5 keV.

To solve the linear equation it is necessary to establish that the determinant of the matrix A, which stores the mass attenuation coefficients, is different from zero. Because the difference in the mass attenuation coefficients is small the matrix is ill conditioned and the determinant of the matrix as reported by several scientists is very small. (See Lehman, et al., "Generalized image combinations in dual KVp digital radiography." *Med. Phys.* 8. 1981 (659–667); Kotzki, et al., "Theoretical and experimental limits of triple photon energy absorptiometry in the measurement of bone mineral." *Phys. Med. Biol.* 36(4), 429–437, 1991; Sutcliffe, "A review of in vivo experimental methods to determine the composition of the human body." *Phys. Med. Biol.* 41, 1996 (791–833).)

For example, when calculating the determinant of the matrix at 1 keV interval, matrix A, which stores the mass attenuation coefficients for bone, muscle and adipose tissue, respectively, at the energies 36.5, 37.5 and 38.5 keV is:

$$\begin{bmatrix} 0.3799 & 0.2891 & 0.2505 \\ 0.3668 & 0.2821 & 0.2467 \\ 0.3543 & 0.2754 & 0.2429 \end{bmatrix}$$

The determinant of the matrix is $-1.58427 \cdot 10^{-7}$.

Increasing the energy interval to 6 keV, which corresponds to mass attenuation coefficients values at the energies 36.5, 42.5 and 48.5 keV matrix A is now:

$$\begin{bmatrix} 0.3799 & 0.2891 & 0.2505 \\ 0.3104 & 0.2516 & 0.2293 \\ 0.2631 & 0.2250 & 0.2129 \end{bmatrix}$$

The calculated determinant of the matrix shown above is $-1.437997 \cdot 10^{-6}$.

A program was written in True Basic using an IBM computer to calculate the areal densities of the phantom components, matrix X. Nevertheless, persons skilled in the art to which the invention relates will readily be capable of writing or otherwise providing such a program in other languages or for use on other computer systems. The program employs a guessing routine to minimize the difference between guess values and measured values of the fractional logarithmic transmissions. The fractional logarithmic transmissions through the phantoms of three components that were measured as described above in accordance with another specific underpinning of the invention, were used as the input [B] matrix. Matrix [A] is the two dimensional matrix representing the mass attenuation coefficients of phantom components. The program allows the user to select the energy interval. Starting with the lowest energy in the energy range of interest (36.5 keV), the next energy is 36.5 keV plus the selected energy interval, and the third is 36.5 keV plus two intervals. When the energy reaches the highest value of the selected energy range (57.5 keV) the loop routine takes it back to the lowest value of energy until the twenty two solutions are calculated. For example, when the selected energy interval is 4 keV, the first row in matrix A stores mass attenuation coefficients for bone, muscle and adipose tissue at the energies of 36.5 keV, second row at the energies of 40.5 keV and third at the energy of 44.5 keV. In the second set of equations, the first row stores the values of mass attenuation coefficients at the energy of 40.5 keV, the second row at the energy of 44.5 and third at the energy of 48.5 keV. In this program, twenty two sets of equations were calculated.

The sets of twenty two equations are first solved using the Cramer's rule and the calculated twenty-two values of areal densities of the phantom components are averaged. When solving the equations using Cramer's method, some solutions are obtained which do not make physical sense, as some of the calculated areal densities have negative values. Although, the calculated average values of areal density of the phantom components are sometimes negative their sum is always very close to the calculated values of the sum of the areal densities of the phantoms. The real value of the sum of the phantom areal densities was calculated as $X_b + X_s + X_f$. Phantom 1 contains 20 cm of muscle simulating component, 1 cm of bone and 3 cm of adipose tissue. This corresponds to 21.24 g/cm$^2$ of areal density of muscle; 1.084 g/cm$^2$ of bone and 2.901 g/cm$^2$ of adipose tissue. When solving a set of linear equations using Cramer's rule and an energy interval of 4 keV, the calculated values of areal densities for the first set of equations are +20.411 g/cm$^2$, −0.542 g/cm$^2$, and +5.837 g/cm$^2$ for muscle, bone and adipose tissue, respectively. The sum of the calculated areal density using the Cramer's method is 25.706 and the calculated true value is 25.225 g/cm$^2$. Phantom 5 contains 10.62 g/cm$^2$ of areal density of muscle, 1.084 and 2.901g/cm$^2$ of bone and adipose tissue, respectively. The calculated values of areal density using the same, 4 keV energy intervals for the first set of equations and the Cramer's method are 13.243, 0.224 and 1.176 g/cm² for muscle, bone and fat, respectively. The sum of the calculated areal density is 14.643 g/cm² with true value being 14.605 g/cm².

For every phantom, the fraction of areal density of the phantom components as a fraction of the sum of areal densities of muscle, adipose tissue and bone was calculated as:

$$f_s = \frac{X_s}{X_s + X_b + X_f} \quad (18)$$

$$f_b = \frac{X_b}{X_s + X_b + X_f} \quad (19)$$

and the fraction of adipose tissue can be calculated as $f_f = 1 - (f_s + f_b)$.

where: $f_s$, $f_b$ and $f_f$ are the fractions of muscle, bone and adipose tissue, respectively. $X_s$, $X_b$ and $X_f$ are the areal densities of the muscle, bone and adipose tissue, respectively. Areal density, as mentioned previously, is the product of the physical density and thickness of the phantom component transverse by the photons in g/cm².

For the five phantoms used in this project, the muscle fraction ranges from 0.669 to 0.842, the adipose tissue fraction ranges from 0.114 to 0.286 and the bone fraction ranges from 0.043 to 0.103. For example, the areal density of muscle in phantom 1 is 21.24 g/cm², and the sum of areal density of all phantom components is 25.225 g/cm². This corresponds to the fraction of muscle in this phantom of 0.842. The same phantom contains 1.084 g/cm² of bone, which corresponds to the fraction of bone in this phantom of 0.043. The fraction of the adipose tissue is calculated by subtracting from one the sum of fractions of muscle and bone fractions.

For each phantom, the program assigns the range of the fraction of areal density of the phantom components by adding and subtracting 0.01 from the calculated fraction. For example the fraction of the bone in phantom 1 is 0.043. The calculated range varies form 0.033 to 0.053. Knowing that fraction of 0.043 corresponds to 1.084 g/cm², the fraction of 0.033 corresponds to the areal density of the bone of 0.832 g/cm² and fraction of 0.053 to 1.336 g/cm². The range of 0.7–1.4 g/cm² of bone mineral density covers the normal spine and femoral neck scanning. The change of the fraction by only 0.01 in both directions change the fraction of the bone by 23% in both minus and plus direction.

In the calculation loop of the computer program, the first estimate is calculated as the sum of the products of the fractions of the phantom components and calculated sum of the areal densities and mass attenuation coefficient of the phantom components at selected energies. The value of the fraction is perturbed in 0.001 step in both minus and plus directions within calculated fraction range to achieve the minimum difference between the calculated sum of the products of the areal densities and mass attenuation coefficients and measured fractional logarithmic transmission. Measured logarithmic transmission for each phantom at the selected energy range (36.5–57.5 keV) is matched to the calculated sum of the products of the fractions of phantom components, mass attenuation coefficients of the components and sum of areal density for that phantom. The program assigns the best fraction for each of the phantom component for which the difference between the sum of the products of these fractions and mass attenuation coefficients of this components and sum of the areal density of the phantom and measured fractional logarithmic transmission is the smallest.

The areal density of the phantom components is calculated as the product of the best fraction of that component and the sum of areal densities.

Figure 11:
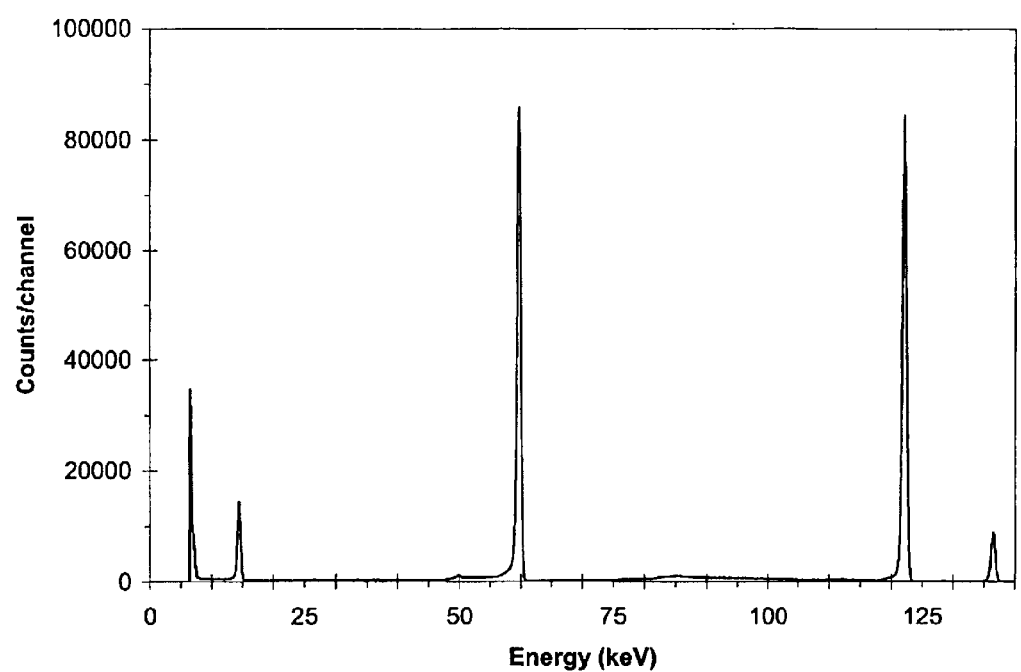
FIG. 11 shows calibration spectra of Co-57 and Am-241 sources used for the calibration of the spectroscopy system.
Figure 12:
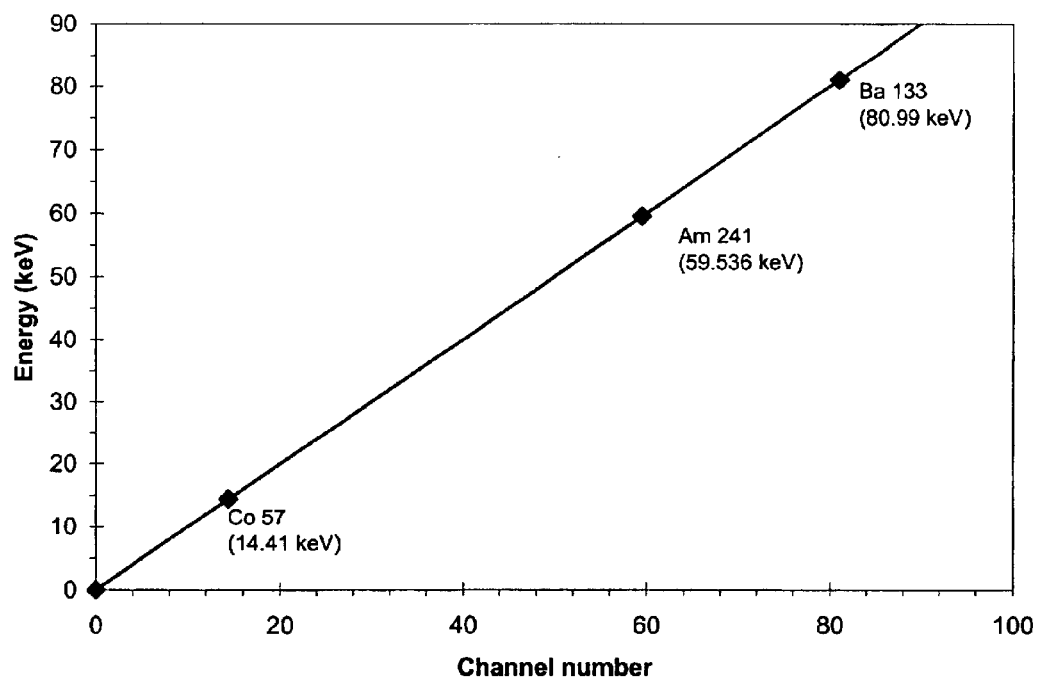
FIG. 12 shows the energies of the Co-57, Ba-133 and Am-241 sources plotted versus channel number.

The results are described below. The calibration spectra of Co-57 and Am-241, plotted on the same graph, are shown in FIG. 11. The channel numbers for Co-57, Am-241 and Ba-133 sources plotted against photon energy in keV are shown in FIG. 12.

Figure 13:
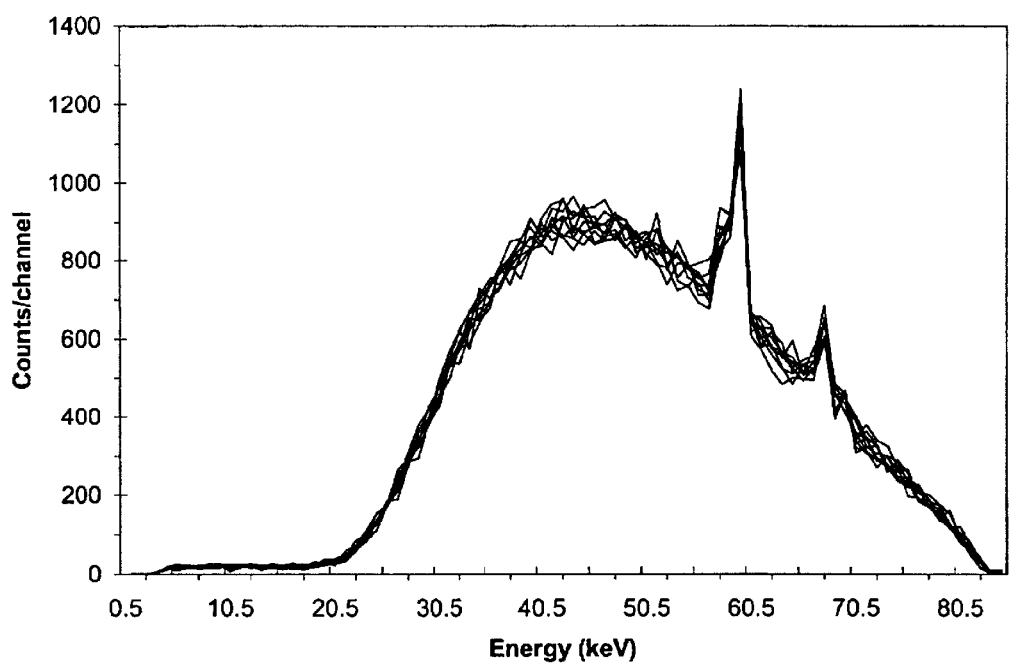
FIG. 13 shows ten x-ray spectra taken at 85 kVp, 0.01 mA and 50 second duration plotted on the same graph. This was done to demonstrate the reproducibility of the x-ray spectra measurements.

Ten of the x-ray spectra obtained in 50 second exposures are shown in FIG. 13. The coefficients of variation were calculated for selected energies in order to determine the variability of the mean. The mean number of counts, standard deviation and coefficient of variation are shown in the table of FIG. 14. The average value of coefficient of variation calculated from the formula 1 is 0.0109.

Figure 15:
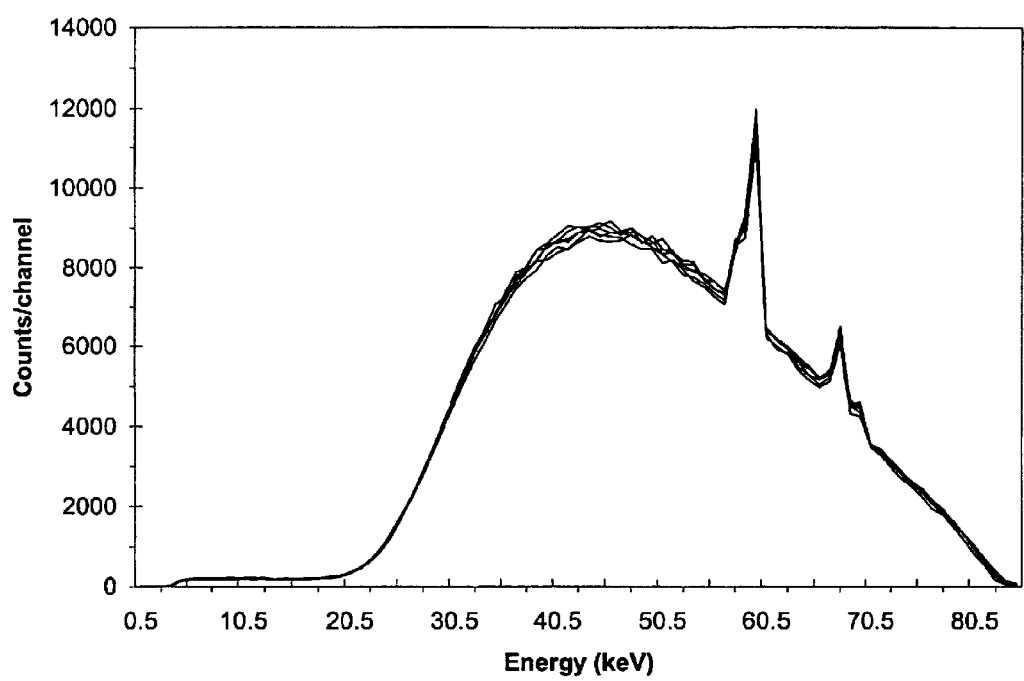
FIG. 15 shows ten composite x-ray spectra curves taken at 85 keV, 0.01 mA and 500 second duration plotted on the same graph.

Ten of the 500 seconds spectra, which are ten 50 seconds exposures added are shown in FIG. 15. The table of FIG. 16 shows the standard deviation, coefficients of variation of the 500 seconds exposures. The average value of the calculated coefficient of variation is 0.0039.

Figure 17:
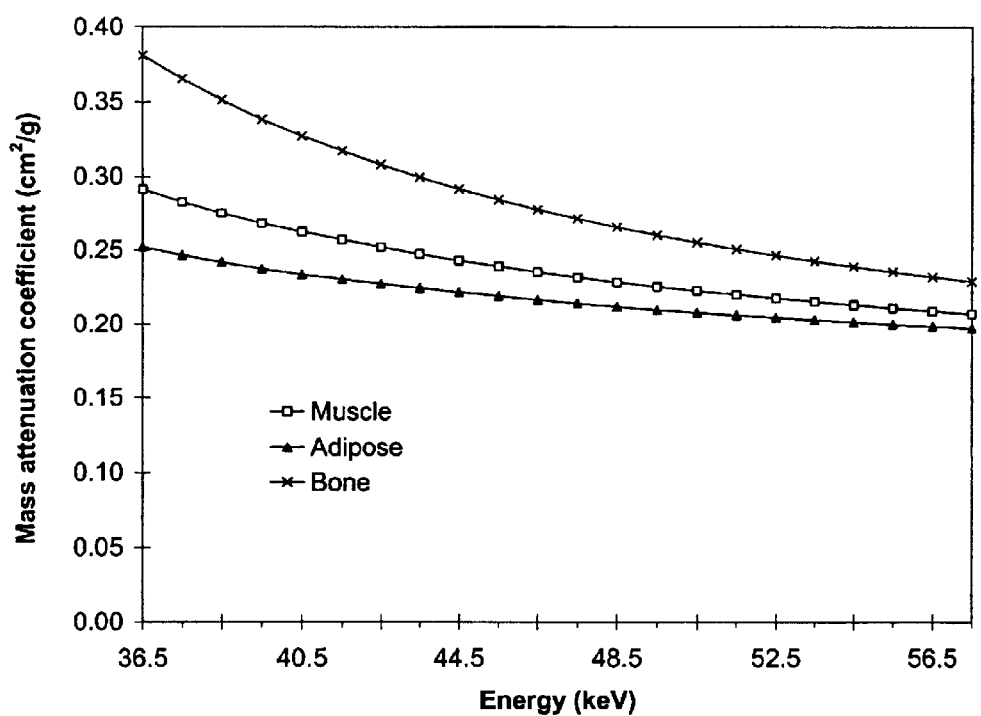
FIG. 17 shows theoretically derived values of the mass attenuation coefficients for muscle, adipose tissue and bone simulating phantoms plotted as the function of energy in the energy range of interest.

FIG. 17 shows the theoretically derived values of the mass attenuation coefficients for muscle, adipose tissue and bone simulating phantoms used in this study plotted as the function of energy in the energy range of interest.

The values of the components of mass attenuation coefficients were taken from Hubbell and interpolated at the middle of the channel at 1 keV intervals. The values of mass attenuation coefficients of tissues calculated from the formula 10 and plotted as the function of energy in the energy range of interest are shown in FIG. 17.

Figure 18:
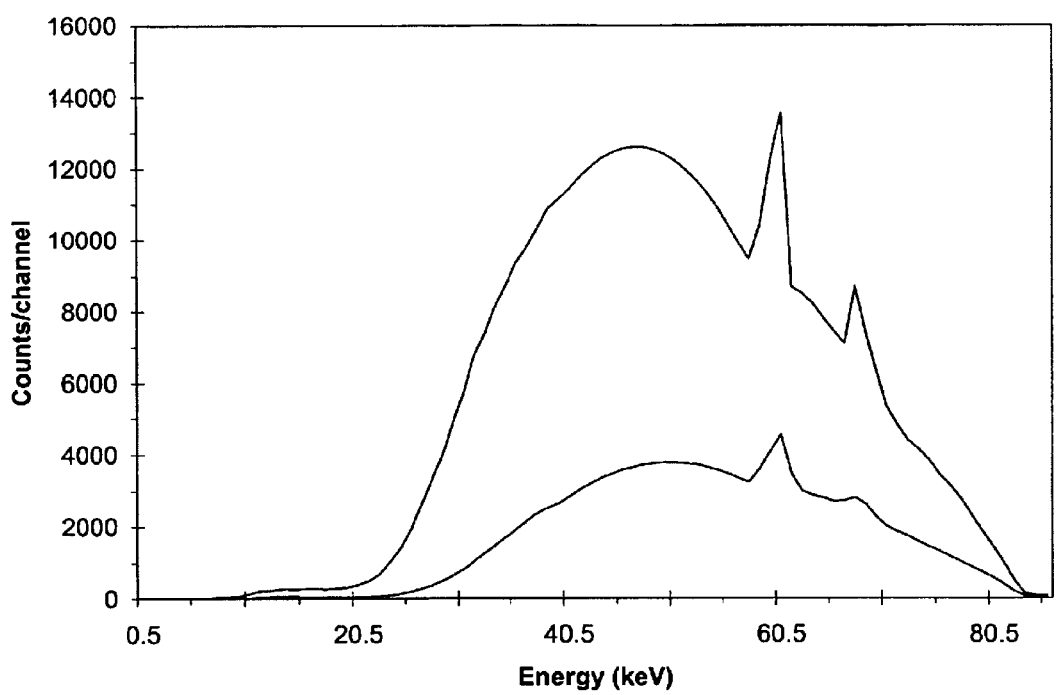
FIG. 18 shows the pulse height distribution of primary and transmitted spectra through 5 cm of muscle simulating phantom. The data was obtained at 85 kVp, 0.011 mA and 500 second duration.
Figure 19:
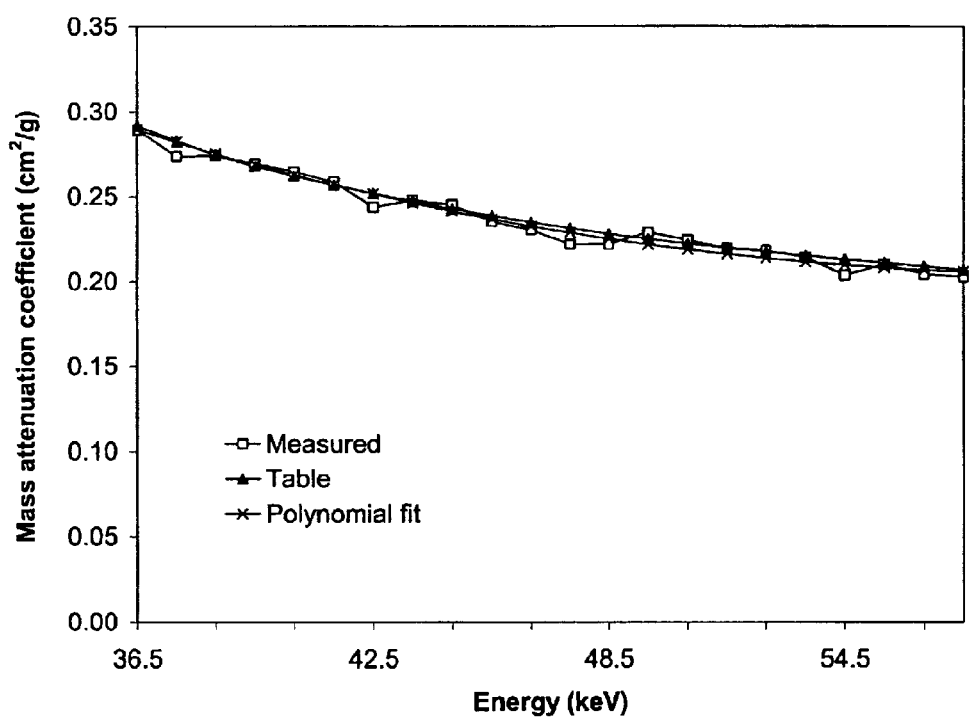
FIG. 19 shows experimentally obtained mass attenuation coefficients for muscle compared with the theoretically determined values calculated from the pulse height distribution photon spectra in FIG. #18 in the energy range of 36.5–57.5 keV.

FIG. 18 shows the primary and transmitted spectra through 5 cm of muscle simulating phantom. In FIG. 19 the experimentally obtained mass attenuation coefficients are compared with theoretically determined values. The measured mass attenuation values were fitted to a second degree polynomial.

The average absolute percent difference between the measured and the table values of the mass attenuation coefficients at 1 keV intervals were calculated from the formula below:

$$\text{Average \% difference} = \frac{100}{N} \sum_{i=1}^{N} \frac{\text{abs}\left[\left(\frac{\mu}{\rho}\right)_{theor.} - \left(\frac{\mu}{\rho}\right)_{exper.}\right]}{\left(\frac{\mu}{\rho}\right)_{theor.}} \quad (20)$$

The average percent difference between the experimentally and theoretically determined values calculated from the formula 20 in the energy range of 36.5–57.5 is 0.91%. The values of experimentally and theoretically derived values of mass attenuation coefficients in the energy range of interest, ratios of experimentally and theoretically derived values and uncertainty in the mass attenuation coefficient per energy channel are shown in the table of FIG. 20. Using Formula 12, the average uncertainty in the mass attenuation coefficient of the muscle simulating phantom is 0.0037 cm²/g.

Figure 21:
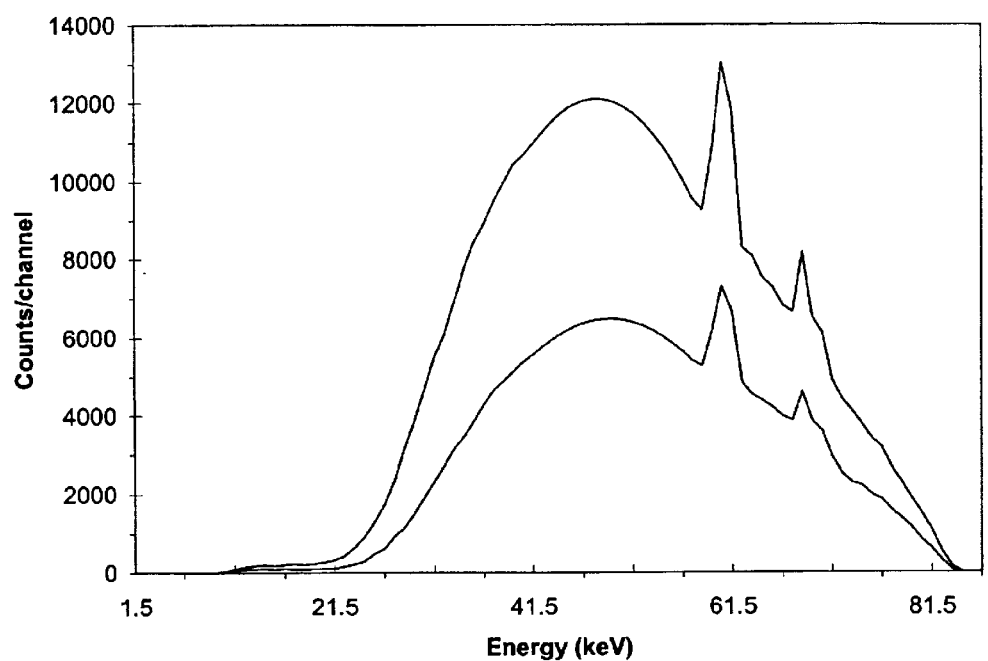
FIG. 21 shows the pulse height distribution of the photons of the primary and transmitted spectra through the 3 cm of adipose tissue simulating phantom. The x-ray spectra were generated at 85 kVp, 0.011 mA and 500 second duration.
Figure 22:
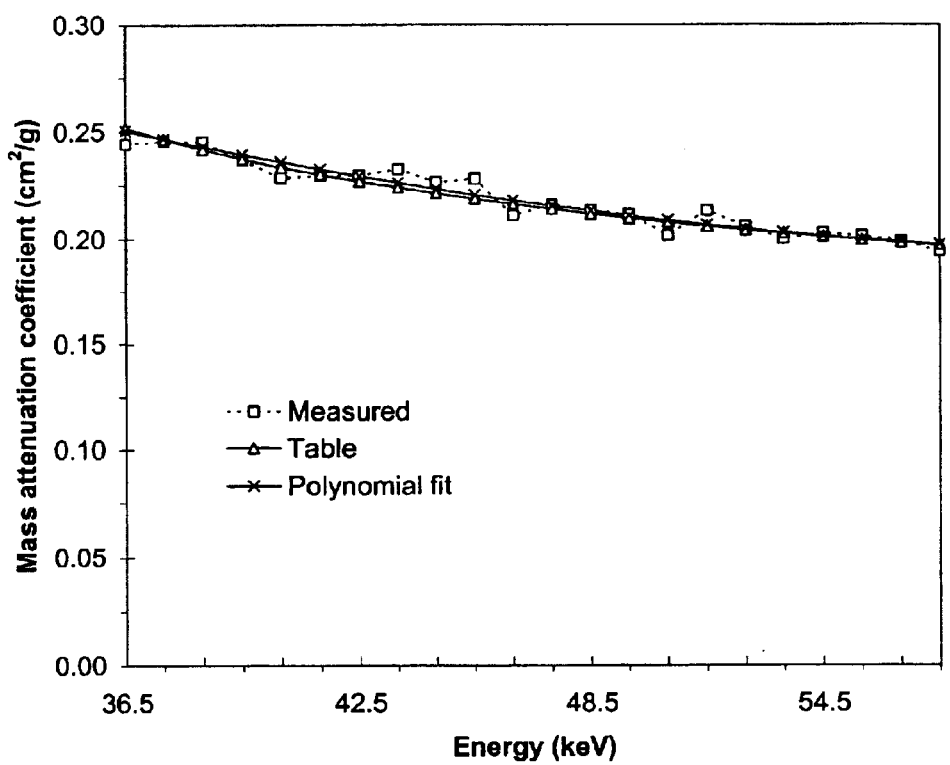
FIG. 22 shows experimentally obtained mass attenuation coefficients for the adipose tissue simulating phantom compared with the theoretically determined values.

The primary and transmitted pulse height distributions through the 3 cm of the adipose tissue simulating phantom are shown in FIG. 21. The measured, theoretically derived and second degree polynomial fitted to the measured data is shown in FIG. 22. The calculated average percent difference between the experimentally and theoretically determined values calculated from equation 12 was 0.54%. The average calculated uncertainty in the experimentally determined values was 0.0056 cm$^2$/g. The table of FIG. 23 shows the values of experimentally and theoretically derived values of mass attenuation coefficients in the energy range of interest, ratios of experimentally and theoretically derived values and uncertainty in the mass attenuation coefficient per energy channel.

Figure 24:
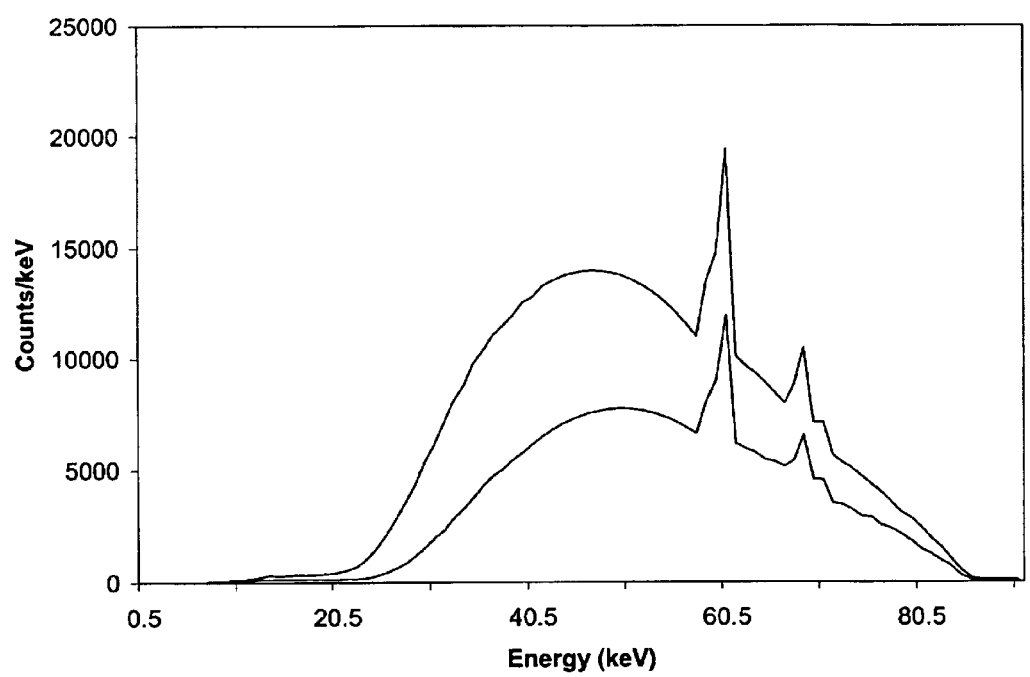
FIG. 24 shows the pulse height distribution of the photons of the primary and transmitted spectra through 2 cm of bone tissue simulating phantom obtained at 86.5 kVp, 0.01 mA and 500 second duration.
Figure 25:
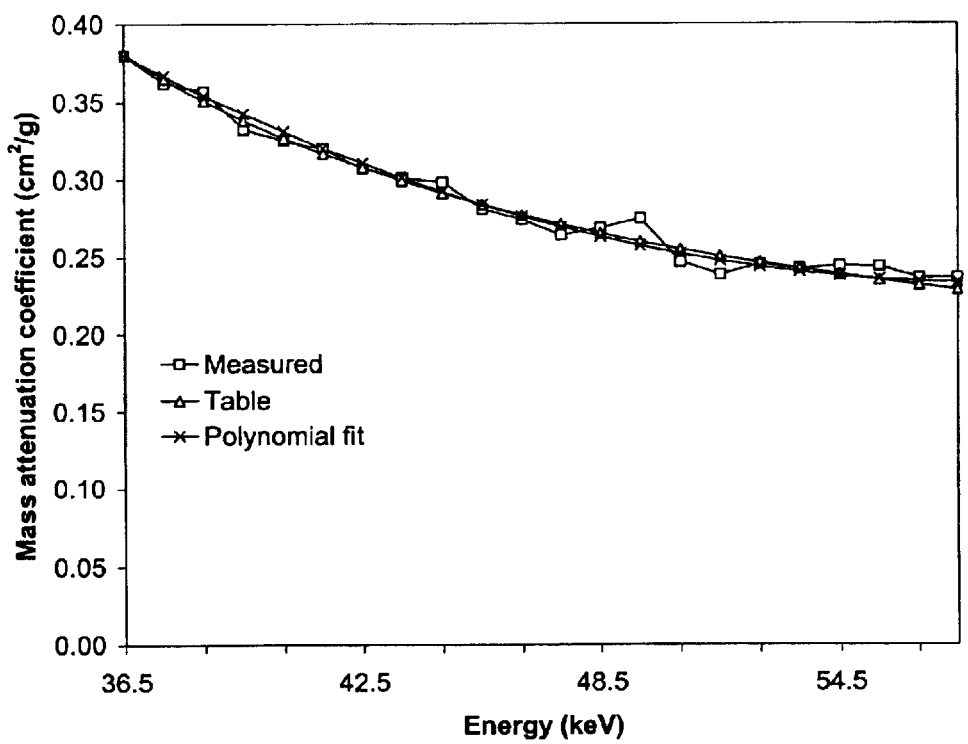
FIG. 25 shows experimentally obtained mass attenuation coefficients of the bone tissue simulating phantom compared with the theoretically derived values.

The primary and transmitted pulse height distributions through 2 cm of the bone simulating tissue are shown in FIG. 24. Comparison of measured, theoretically derived, and second degree polynomial fitted to the measured data is shown in FIG. 25. The calculated average percent difference between the experimentally and theoretically determined values was 0.81%. The average calculated uncertainty in the experimentally determined values was 0.0069 cm$^2$/g. The table of FIG. 26 shows the values of experimentally and theoretically derived values of mass attenuation coefficients in the energy range of 36.5–57.5 keV, ratios of experimentally and theoretically derived values and uncertainty in the mass attenuation coefficient per energy channel.

The following results were obtained for measurements through three component phantoms and calculation of the fractional logarithmic transmissions.

Bone 100 (Computerized Imaging Reference Systems, Inc.) was used in all of the phantoms assembled from the tissues simulating materials. Bone 100 corresponds to 100 mg/cm$^3$ of hydroxyapatite ($Ca_{10}(PO_4)_6(OH)_2$). A range of hydroxyapatite of trabecular bone from 50–200 mg/cm$^3$ is typical for spinal bone mineral measurements.

Figure 27:
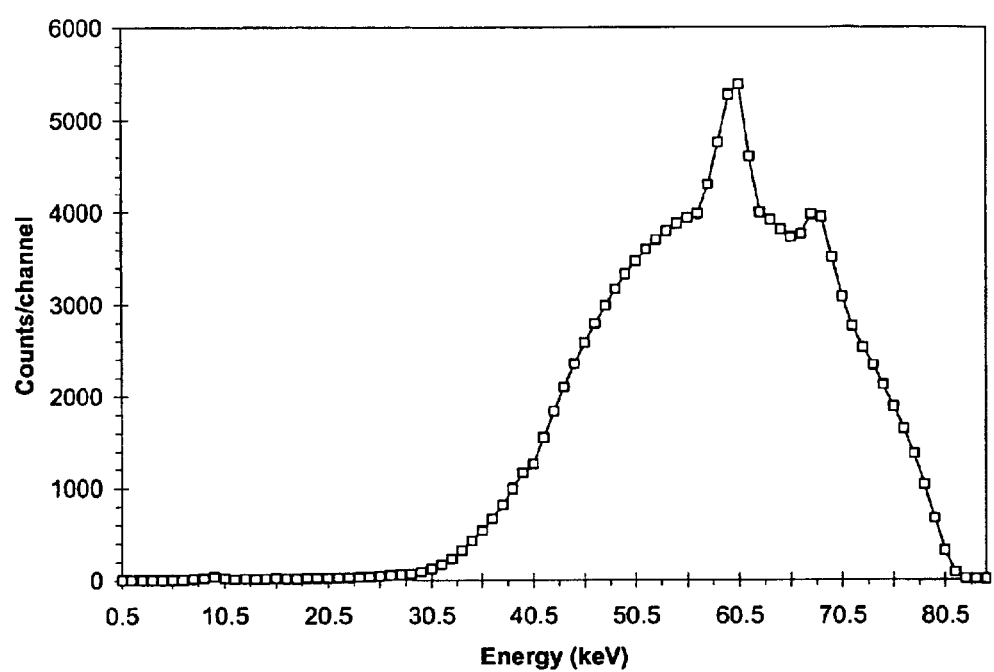
FIG. 27 shows the pulse height distribution of the photon spectrum transmitted through 20 cm muscle, 3 cm adiopose and 1 cm bone simulating phantom. The spectrum was generated at 82 kVp, 0.343 mA and 750 second duration.
Figure 28:
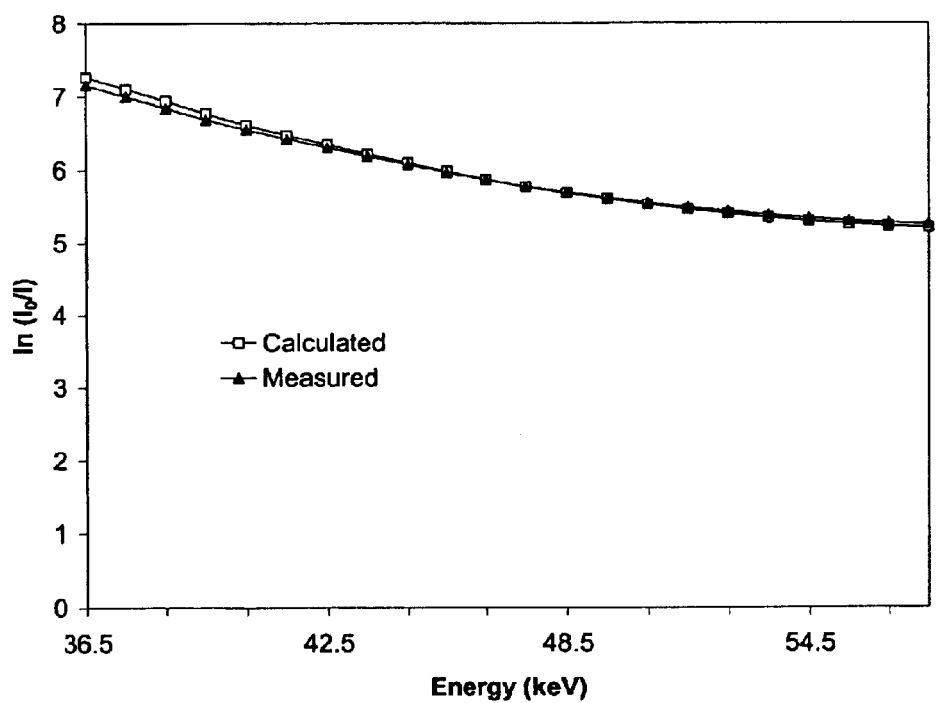
FIG. 28 (Phantom 1) shows the comparison of calculated values of the sum of the products of the mass attenuation coefficients and areal densities for three components of a first phantom and measured fractional logarithmic transmissions.

Phantom 1 contains 20 cm of the muscle simulating material, 3 cm of adipose tissue and 1 cm of bone. This corresponds to areal densities of 21.24 g/cm$^2$ of muscle, 2.901 g/cm$^2$ of adipose tissue and 1.084 g/cm$^2$ of bone, respectively. The overall thickness of the phantom was 24 cm. The spectrum transmitted through the phantom is shown in FIG. 27. Comparison of the calculated values of sum of the products of areal densities and mass attenuation coefficients (right side of equation 13) and measured values of fractional logarithmic transmission (left side of equation 13) is shown in FIG. 28. The average percent difference calculated from formula 20 at the energy range of 36.5–57.5 was 0.63%.

Figure 29:
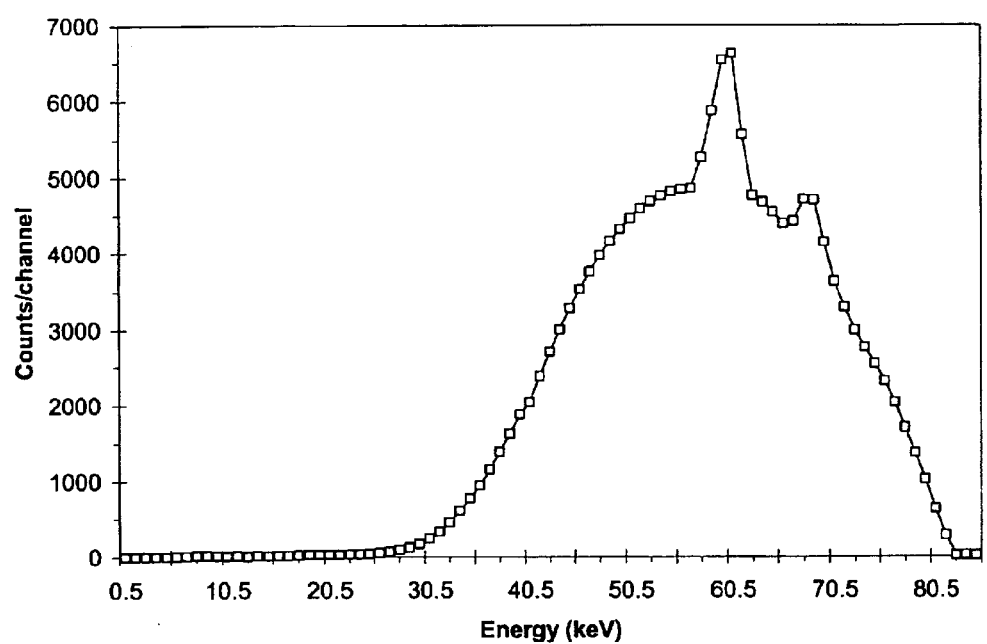
FIG. 29 shows the pulse height distribution of the photon spectrum transmitted through 15 cm muscle, 3 cm adiopose and 1 cm bone simulating phantom. The spectrum was generated at 82 kVp, 0.152 mA and 750 second duration.
Figure 30:
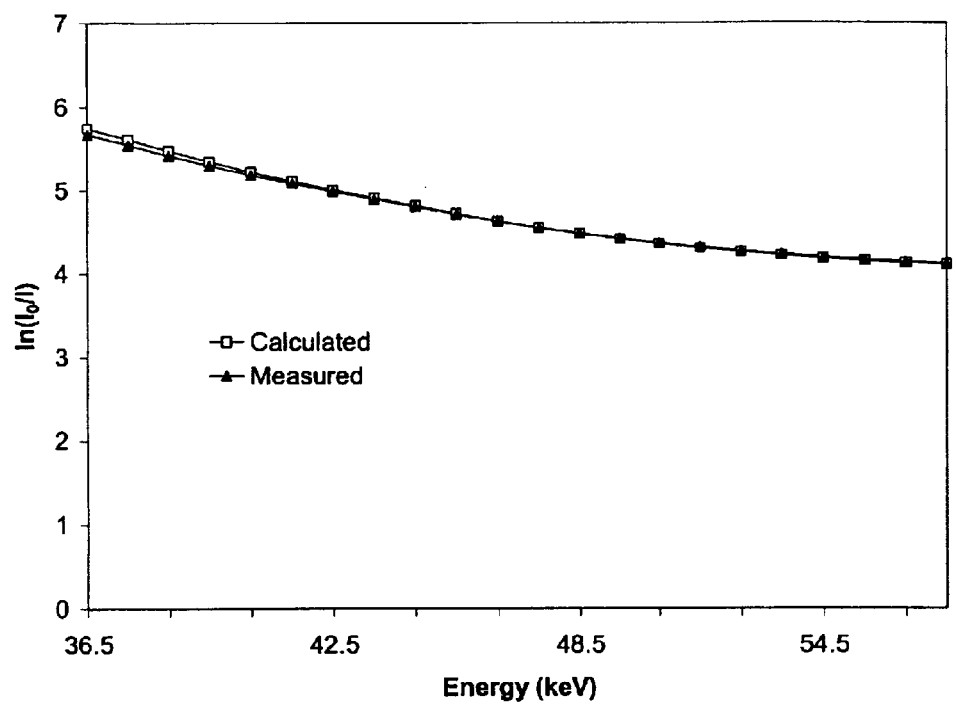
FIG. 30 (Phantom 2) shows a comparison of calculated values of the sum of products of the mass attenuation coefficients and areal densities and measured fractional logarithmic transmissions.

To examine the influence of body thickness on the measured bone mineral value, the second phantom contained 15 cm of muscle and the same amount of bone and adipose tissue as the previous phantom. This corresponds to areal densities of 15.93 g/cm$^2$ of muscle, 2.901 g/cm$^2$ of adipose tissue and 1.084 g/cm$^2$ of bone. The spectrum transmitted through the phantom is shown in FIG. 29. The comparison between the calculated sum of the products of the mass attenuation coefficients and areal densities (left side of equation 13) of the three components phantom and fractional logarithmic transmission (right side of equation 13) is shown in FIG. 30. Calculated from formula 20, the average percentage difference between the calculated and measured value is 0.26%.

FIG. 30 shows the comparison of calculated values of the sum of products of the mass attenuation coefficients and areal densities for phantom 2 and measured fractional logarithmic transmissions.

Figure 31:
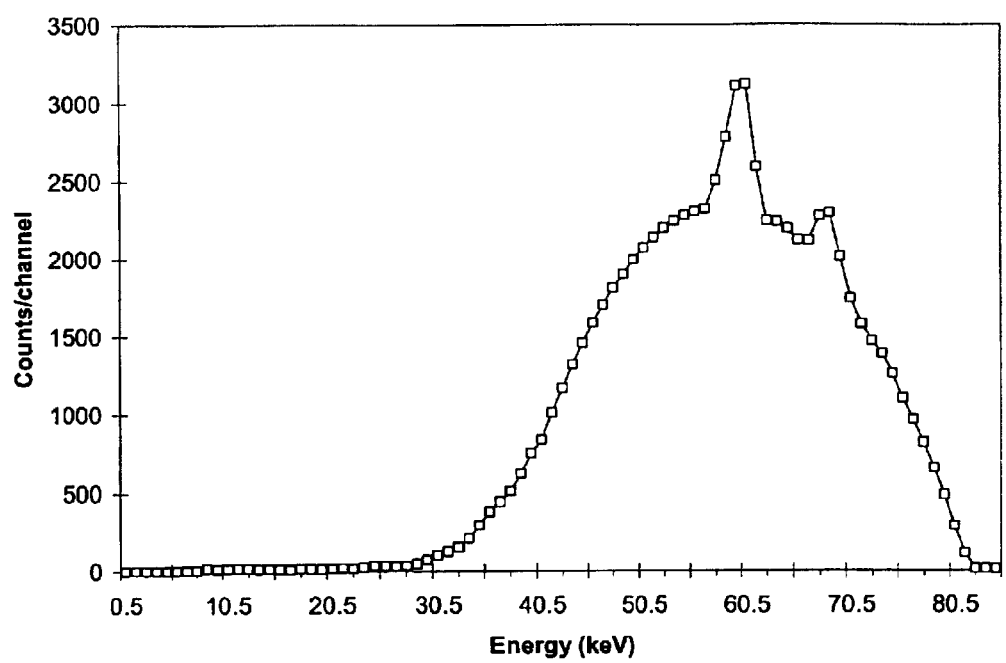
FIG. 31 shows the pulse height distribution of the photon spectrum transmitted through 15 cm muscle, 7 cm adiopose and 1 cm bone simulating phantom. The spectrum was generated at 82 kVp, 0.15 mA and 750 second duration.
Figure 32:
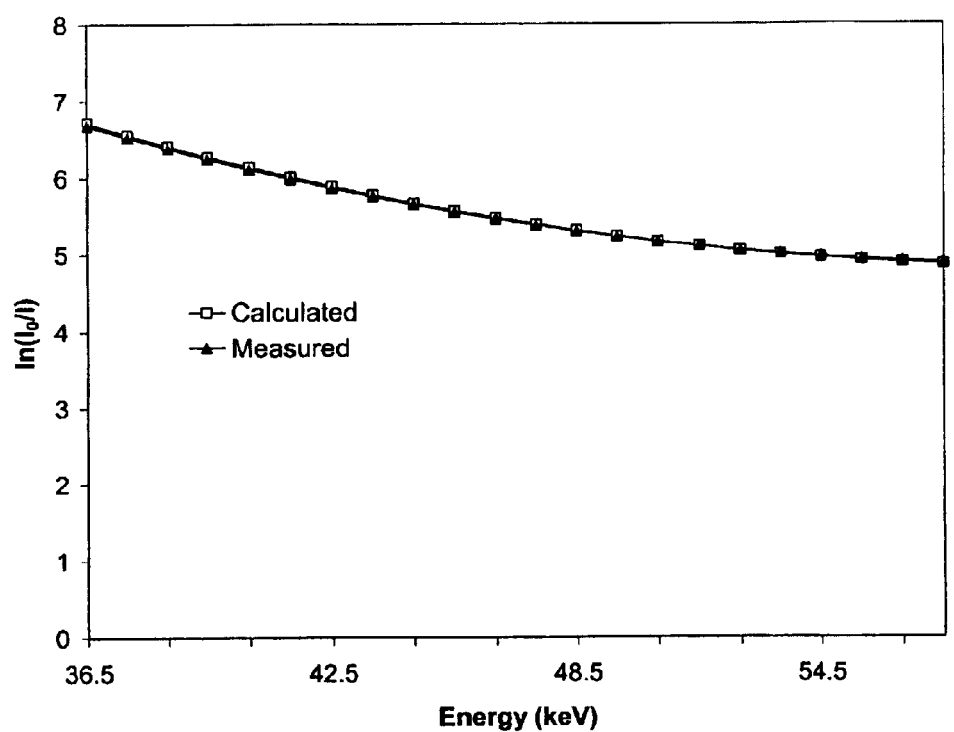
FIG. 32 (Phantom 3) shows the comparison of calculated values of the sum of products of the mass attenuation coefficients and areal densities and measured fractional logarithmic transmissions.

Phantom three contains 15 cm of muscle, 7 cm of adipose tissue and 1 cm of bone. This corresponds to areal densities of 15.93 g/cm$^2$ of muscle, 6.769 g/cm$^2$ of adipose tissue and 1.084 g/cm$^2$ of bone. The pulse height distribution of the photons spectrum transmitted through the phantom is shown in FIG. 31. Calculated from equation 13, the sum of the products of the mass attenuation coefficients and areal densities of the phantom components (left side of equation 13) are compared with the logarithmic transmission factor in FIG. 32. The average percent difference calculated from Formula 13, over the energy range of interest is 0.47%.

Figure 33:
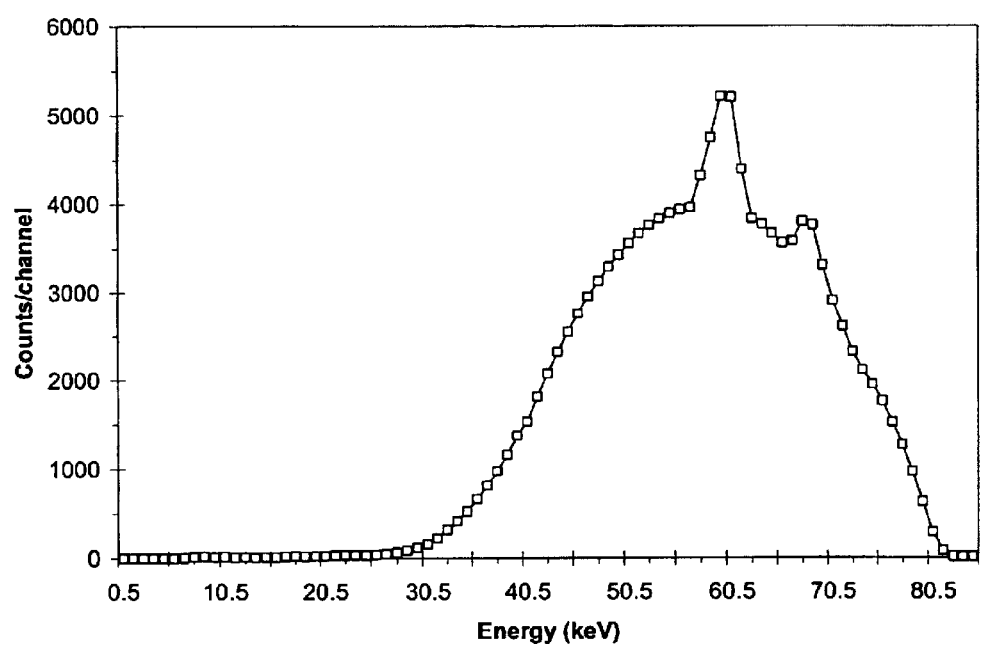
FIG. 33 shows the pulse height distribution of the photon spectrum transmitted through 15 cm muscle, 3 cm adipose and 2 cm bone simulating phantom. The spectrum was generated at 82 kVp, 0.144 mA and 750 second duration.
Figure 34:
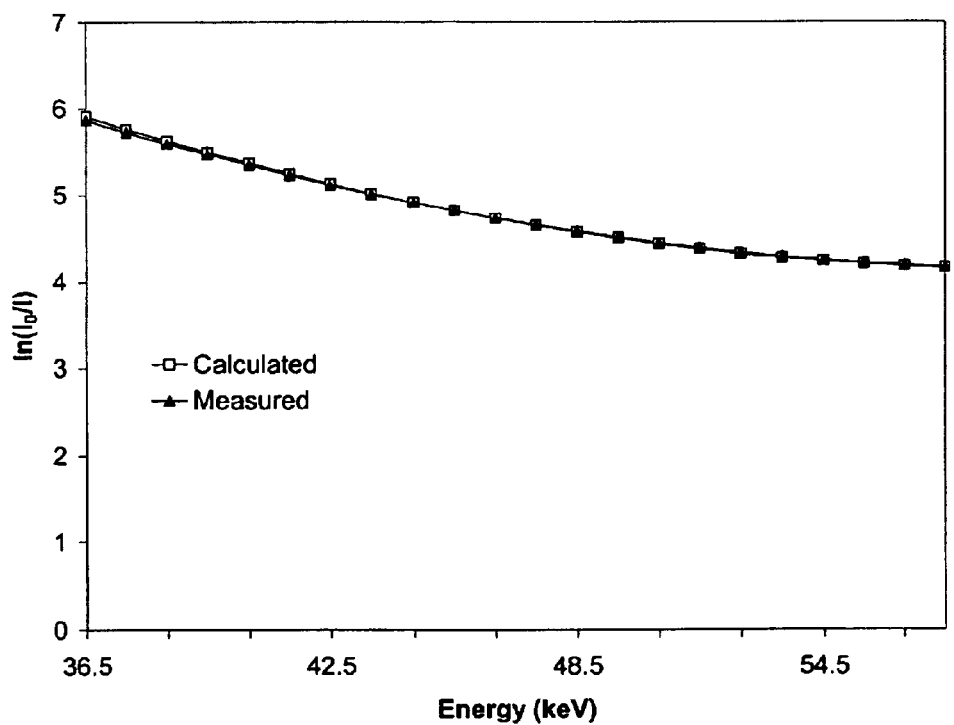
FIG. 34 (Phantom 4) shows the comparison of calculated values of the sum of products of the mass attenuation coefficients and areal densities and measured fractional logarithmic transmissions.

Phantom four contains 15 cm of muscle, 3 cm of adipose tissue and 2 cm of bone, which corresponds to the areal densities of 15.93 g/cm$^2$ for muscle, 2.901 g/cm$^2$ for adipose tissue and 2.168 g/cm$^2$ for bone. The pulse distribution of photons transmitted spectrum through the phantom is shown in FIG. 33. The comparison of the calculated sum of the products of the mass attenuation coefficients and areal densities of phantom components and fractional logarithmic transmission is shown in FIG. 34. Calculated from the equation 20, the average difference between measured and calculated values is 0.21%.

Figure 35:
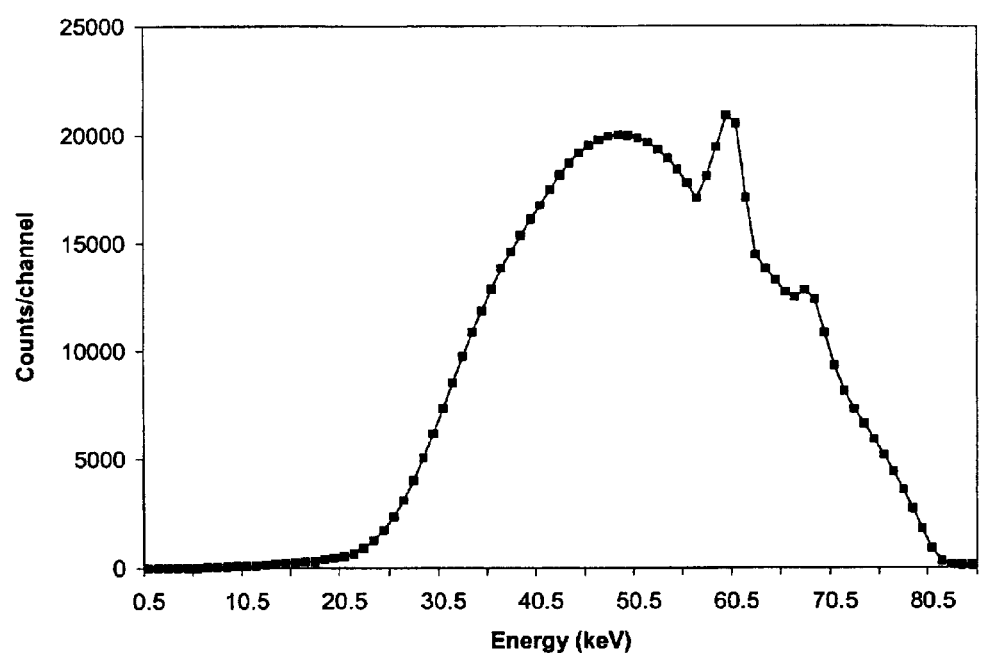
FIG. 35 shows the pulse height distribution of the photon transmitted spectrum through 0.1 mm of copper (Cu).

For the four phantoms described above the primary spectrum was obtained at the lowest tube current of 0.01 mA, at the same kVp as the phantoms measurements. To reduce photon fluence the pulse height photon spectrum was measured with 0.1 mm of copper (Cu) in the beam. The pulse height distribution of photons transmitted through 0.1 mm of Cu is shown in FIG. 35. The measured pulse height photon spectrum was corrected for 0.1 mm Cu attenuation and the ratio of tube current for each phantom. Tube currents for the phantom measurement were increased to 0.343 mA for phantom 1, 0.152 mA for phantom 2, 0.15 mA for phantom 3 and 0.144 mA for phantom 4. The dead time for the phantom measurements and the primary beam displayed on the multichannel analyzer was 0–1%. An exposure of 750 seconds was performed for each measurement.

FIG. 35 shows the pulse height distribution of photons transmitted spectrum through 0.1 mm of copper (Cu).

Figure 36:
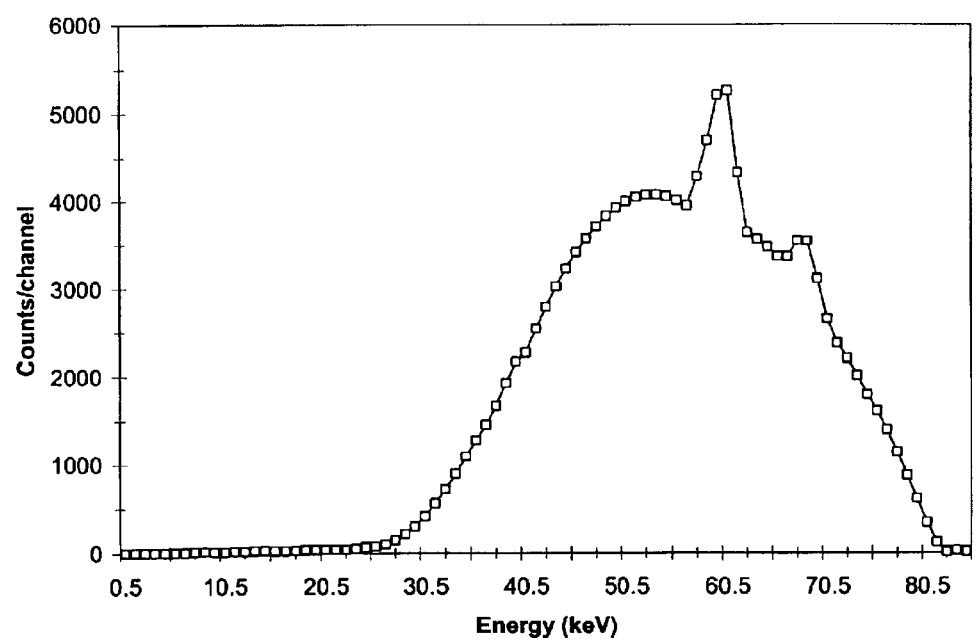
FIG. 36 shows the pulse height distribution of the photons spectrum transmitted through 10 cm muscle, 3 cm adiopose and 1 cm bone simulating phantom. The spectrum was generated at 82 kVp, 0.029 mA and 1000 second duration.
Figure 37:
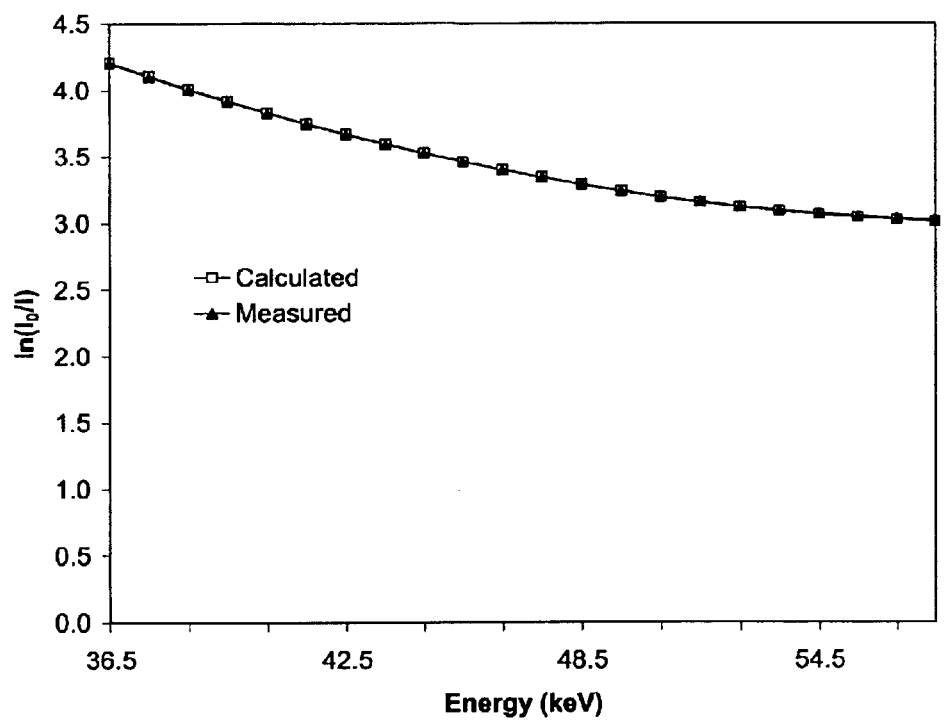
FIG. 37 (Phantom 5) shows a comparison of calculated values of the sum of the mass attenuation coefficients and areal densities and measured fractional logarithmic transmissions.

Phantom five contains 10 cm of the muscle, 3 cm of adipose and 1 cm of bone. This corresponds to areal densities of 10.62 g/cm$^2$ of muscle, 2.901 g/cm$^2$ of adipose tissue and 1.084 g/cm$^2$ of bone. The pulse height distribution of the photon spectrum transmitted through the three components phantom is shown in FIG. 36. The comparison of the calculated sum of the products of mass attenuation coefficients and the areal densities of phantom components and the fractional logarithmic transmission is shown in FIG. 37. Calculated from equation 20, the average difference between calculated and measured values in energy range of 36.5–57.5 keV was 0.36%. The measurement of the primary beam for this phantom was performed with a tube current of 0.01 mA 82 kVp and 7 cm of acrylic in the beam. During the transmitted beam measurements 7 cm of acrylic was added to the beam. The exposure time 1000 second duration was used for both primary and phantom spectra. During the phantom measurement, the tube current was increased to 0.029 mA.

FIG. 36 shows the pulse height distribution of the photons spectrum transmitted through 10 cm soft tissue, 3 cm adipose and 1 cm bone simulating phantom. The spectrum was generated at 82 kVp, 0.029 mA and 1000 second duration. Additionally, 7 cm of the acrylic in the x-ray beam.

FIG. 37 shows a comparison of calculated values of the sum of the mass attenuation coefficients and areal densities for phantom 5 and measured fractional logarithmic transmissions.

When calculating the sum of areal density of the phantoms using the Cramer's method, as previously stated, the sum of the calculated areal density is close to the sum of true values. The table of FIG. 38 shows the sum of the areal densities of the phantoms, and the calculated average values using the Cramer's method. The values were obtained by increasing the energy intervals from 1 keV to 10 keV. The Cramer's method overestimates the sum of the areal densities for all the phantoms. Increasing the energy interval from 1 keV to 10 keV the percent difference between the calculated average sum of the areal densities and the true values of sum of the areal densities is 2.75% for phantom one, 0.21% for phantom two, 3.05% for phantom three, 1.7% for phantom four and 1.75% for phantom five. The standard deviation of the mean values is 0.082, 0.028, 0.154, 0.052 and 0.058 g/cm$^2$ for phantom 1, 2, 3, 4 and 5, respectively.

Using the computer program and increasing the energy interval from 1 to 10 keV the areal densities and the average values for muscle, adipose tissue and bone were calculated for each phantom and are shown in FIGS. 39, 40 and 41, respectively. Increasing the energy interval from 1 to 10 keV the average values of the areal densities of the muscle is overestimated by 2.26% for phantom 1, 0.11% for phantom 2, 3.18% for phantom three, 1.57% for phantom four and 1.17% for phantom five. The calculated standard deviation of the average value is 0.069, 0.021, 0.089, 0.047 and 0.030 g/cm$^2$ for phantoms 1, 2, 3, 4 and 5 respectively.

The mean value of the calculated areal densities of the adipose tissue, shown in FIG. 40, is overestimated by 7.21% for phantom 1, 3.20% for phantom 2, 5.11% for phantom 3, 4.98% for phantom 4 and 6.12% for phantom 5. The standard deviation of the calculated mean is 0.010 g/cm$^2$ for phantom 1, 0.023 g/cm$^2$ for phantom two, 0.058, 0.016 and 0.038 g/cm$^2$ for phantoms three, four and five respectively.

Increasing the energy intervals from 1 to 10 keV the calculated values of the areal densities of the bone mineral and the mean values for each phantom are shown in FIG. 41. The calculated average value of the areal density of the bone is higher by 0.42% a true value for the phantom 1. The average calculated value of the bone mineral density is underestimated by 6.31%, 2.71%, 1.71% and 4.21% for phantoms 2, 3, 4 and 5, respectively. The calculated standard deviation of the mean value is 0.003, 0.017, 0.017, 0.012 and 0.010 g/cm$^2$ for phantoms 1, 2, 3, 4 and 5, respectively.

The table of FIG. 38 shows the sum of areal densities of the phantoms calculated using Cramer's method.

The table of FIG. 39 shows calculated values of muscle areal densities.

The table of FIG. 40 shows the calculated values of adipose tissue areal densities.

The table of FIG. 41 shows the calculated values of bone areal densities.

For the accurate determination of bone mineral density using the dual or triple energy method, the determination of mass attenuation coefficient of body components is the first step in the measurements. The measured values of mass attenuation coefficients of phantoms stimulating muscle, adipose tissue and bone were in good agreement with theoretically calculated values. For the twenty two energy channels used in this study, the ratio of the measured and theoretically derived values for the soft tissue varied from 0.982 to 1.004 and the average percent difference was 0.91%. For the adipose tissue, the ratio of the measured and theoretically derived values varied from 0.994 to 1.011 and the average percent difference of the measured values was 0.54%. The ratio of the measured and theoretically derived values for bone varied from 0.989 to 1.013 and the average percent difference of the measured values was 0.81%. Considering the tolerance in the thickness of the phantom measurements, 0.02 mm, all measured mass attenuation coefficients were within an acceptable limit.

All the assembled phantom components simulated the values typically encountered in measurements of bone mineral in the spine and femoral neck.

For the measurement of the primary spectrum, the number of photons detected in different energy channels of the continuous x-ray spectrum varied from $1 \cdot 10^5$ to $9 \cdot 10^5$. The number of photons transmitted through different phantoms varied from $1 \cdot 10^3$ to $4 \cdot 10^3$. The calculated average percent difference between the calculated sum of the products of the mass attenuation coefficients and areal densities of the phantoms and measured fractional logarithmic transmission varies from 0.21% to 0.63%. There are several sources of error in the measurements of transmitted spectrum, but the most fundamental are the statistical fluctuation in transmitted intensity.

When the photon absorptiometry method is used with less than three photon energies, the approximation of uniform adipose tissue distribution at the measurement site is used. The accuracy error, which results from the dual energy methodology, has been reported as high as 10%. (Michael, et al., "Monte Carlo modeling of an extended DXA technique." *Phys. Med. Biol.* 43, 2583–2596, 1998). The reported precision of DXA is around 1%, but the results of bone mineral density obtained by different three manufacturers of dual x-ray absorptiometry equipment: Norland, Lunar and Hologic vary substantially.

An alternative method of analyzing the three component body without the fat approximation is to use three different photon energies. As stated by several scientists, the triple energy method is less widely used, because the method is complex and requires a larger number of photons to be detected. (See Farrell et al., 1989, Kotzki et. al., 1991) This is the consequence of the small difference in the mass attenuation coefficients for muscle and adipose tissue in diagnostic energy range. The present study method used the continuous x-ray spectrum, measured using a multichannel analyzer and three component phantoms. The measured numbers of photons in the transmitted spectra were approximately the same as the number of transmitted photons used during the dual energy absorptiometry method. The x-ray unit used in this study allows achieving a very low tube current (10 $\mu$A). This was important during the measurements of the primary spectrum, to reduce the pulse pileup. The tube current can be substantially higher during the phantom measurements.

Although the percent differences between the true sum of the products of areal densities and mass attenuation coefficients and measured fractional logarithmic transmissions were relatively small, solving the attenuation equation using Cramer's rule resulted in solutions that were not physically realistic. However, the sum of the solutions always gave the value close to the sum of the areal density of the phantom. For the five phantoms used in this study, changing the energy intervals from 1 to 10 keV, this difference was always less than 5%. This fact was used as the base for the estimating routine in a computer program.

In clinical studies, the spectrum transmitted through the soft tissue adjacent to the bone of the patient will be first measured. For the selected two energies the areal densities of the muscle and adipose tissue will be calculated using dual energy equations. In the next step the spectrum transmitted through the soft tissue and bone will be measured. The fractional logarithmic transmission will be calculated from the spectra over selected energy range. Using the Cramer's method the sum of areal densities will be calculated. The values of the areal density of the bone will be approximated by subtracting from the calculated sum of areal densities the sum of areal densities of muscle and adipose tissue calculated over the area of soft tissue only. The fraction of each component as the fraction of the sum of areal density will be calculated. Knowing that the inhomogeneity in adipose tissue distribution can introduce the error in bone mineral density grater than 10% in AP imaging and even greater in lateral bone mineral measurements the range of the fraction of each component will be calculated by adding and subtracting around 20% to the previously calculated areal densities. The best fractions of each component will be calculated using the computer program described previously in this project.

As previously stated, to solve the linear equation using Cramer's rule the perfect values of fractional logarithmic transmissions should be used. This requires a large number of photons in the primary and transmitted spectra. Accumulating the large number of photons in the primary beam is not a problem, since this spectrum can be obtained earlier and stored in computer memory, but obtaining a large number of photons in the transmitted beam will deliver a substantial dose to the patient. A computer program introduced in this study takes a different approach from the triple energy methods introduced by other scientists. The program calculates the areal density of the phantom components as the products of the best fraction of that component and the sum of areal densities of the phantom. The best fraction is selected from the estimating routine by calculating the minimum difference between the measured fractional logarithmic transmissions and evaluated values of sum of the products of mass attenuation coefficients, fraction and sum of the areal densities of the phantom.

For the five phantoms described above, ranging the energy interval from 1 to 10 keV, the average percent difference between the calculated areal densities of bone and the true values of that densities range from 0.42% for phantom 1 to 6.31% for phantom 2. No correlation was found between measured bone mineral density value and adipose tissue thickness. In the phantoms assembled in this study, bone mineral density was increased from 1.084 g/cm$^2$ to 2.168 g/cm$^2$ (phantom 4), and adipose tissue from 2.901 g/cm$^2$ to 6.769 g/cm$^2$ (phantom 3). The computer program written in specific aim three underestimated the bone areal density value for four of the phantoms. The system will require calibration with more linear changes in areal densities of phantom components.

The spectral information can be obtained by one of two methods. The standard method involves direct measurements using a multichannel pulse height analyzer. This requires expensive specialized equipment, which must be calibrated. The alternative method involves inferring spectral information from attenuation measurements. Deriving the spectrum from the transmission through the patient and increasing thickness of aluminum can be implemented in a clinical setting.

A system and method for using x-ray spectra to determine areal densities of bone, fat and soft tissue in a localized area of a patient has been described. Although the above-described embodiment of the invention relates to a medical use, the invention has a number of non-medical uses, such as monitoring industrial materials for quality control purposes, screening for hazardous materials such as explosives or weapons in baggage and packages for security purposes, and other uses in which it is desired to detect areal density of a composition in a multi-component mixture. It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for determining areal densities of bone, fat and soft tissue in a localized area of a patient, comprising the steps of:
    (a) collecting data defining an x-ray energy transmission curve by scanning the area of the patient at a plurality of points with a collimated x-ray beam and detecting and measuring beam intensity after having passed through the patient at a plurality of different energies at each point;
    (b) selecting from a database of x-ray spectral curves a spectral curve corresponding to the transmission curve defined by the collected data, wherein each spectral curve relates beam energy to beam intensity at each beam energy;
    (c) defining a curve relating a logarithm of a ratio of beam intensity in air divided by the measured beam intensity after passing through the patient for each of a plurality of photon energies in the beam;
    (d) solving a matrix equation for a solution comprising sum totals of the areal densities of bone, fat and soft tissue in response to predetermined mass attenuation coefficients for bone, fat and soft tissue at a group of three selected energies and in response to the logarithmic ratio obtained from the curve at each of the three selected energies;
    (e) repeating step (d) a plurality of times, each time obtaining a solution by solving the matrix equation at a group of three selected energies different from a group at which the matrix equation was previously solved;
    (f) computing an average of the sum total of the areal densities of bone from the solutions obtained in step(e), an average of the sum total of the areal densities of fat from the solutions obtained in step (e), and an average of the sum total of the areal densities of soft tissue obtained in step (e); and
    (g) performing an iterative method to estimate the areal densities of bone, fat and soft tissue in response to the sum totals of the areal densities of bone, fat and soft tissue.

2. The method recited in claim 1, wherein the step of scanning the area of the patient at a plurality of points with a collimated x-ray beam and detecting and measuring the beam intensity after having passed through the patient at a plurality of different energies at each point comprises the step of passing the beam through a plurality of different thicknesses of an attenuative material at each point.

3. The method recited in claim 1, wherein the step of scanning the area of the patient at a plurality of points comprises the step of scanning the patient in a raster fashion along two axes.

4. The method recited in claim 1, wherein the step of selecting from a database comprises the steps of:
    (h) determining x-ray photon energy spectra in air at a plurality of photon energies in the x-ray spectrum as a function of kVp, mA, and transmitted through different filter material placed in the x-ray beam using measurements with a spectrometer system, analytical calculations, Monte Carlo calculations and interpolation to form a database of x-ray spectra in air;
    (i) determining a transmission curve for the spectra determined in step (h) in response to filters of different thicknesses at each point in the patient;
    (j) matching the transmission curve for the x-ray spectra determined in step (h) to transmission curves in the data base to identify an x-ray energy spectrum that is transmitted through the patient at a plurality of points;
    (k) forming a quantity at each useful photon energy, Ei, in the in air and transmitted x-ray spectra which is the logarithm of Io(Ei)/I(Ei) with Io denoting the in air beam and I denoting the transmitted beam;

(l) selecting three energies to a form a 3×3 matrix with each row of the 3×3 matrix equal to the value formed in step (k) at the energy Ei with the 3×3 matrix being filled by the mass attenuation coefficients of soft tissue, fat and bone at the energies Ei selected for each row;

(m) solving for areal density of soft tissue, fat and bone for each set of three energies selected in step (l);

(n) repeating steps (l) through (m) for a plurality of different energies each and forming the sum of the total areal density of soft tissue, fat and bone derived by each solution; and (o) forming an average value of the total areal density of soft tissue, fat and bone by dividing the sum formed in step (n) by the total number of solutions.

5. The method recited in claim 4, wherein the step of performing an iterative method comprises the steps of:

(p) making a first guess as to the areal density of two components with the areal density of the third component derived by subtracting the estimated areal density of two components from a known total areal density;

(q) calculating the quantity recited in step (k) in response to the estimated areal densities of the three components;

(r) in a step-by-step fashion performing the calculation recited in step in (q) and forming a difference between the calculated quantity using the estimated areal densities and the quantity formed in step (d);

(s) forming a total sum of differences for estimated areal densities;

(t) repeating steps (p) through (s) a plurality of times using different estimates of the individual areal densities and forming the sum of the total differences each time; and (u) selecting a set of areal densities having the smallest total sum difference between two curves as characterizing the correct or true areal densities of soft tissue, fat and bone at that location.

* * * * *